(12) United States Patent
Blair

(10) Patent No.: US 11,464,493 B2
(45) Date of Patent: Oct. 11, 2022

(54) ULTRASOUND MARKER DETECTION, MARKERS AND ASSOCIATED SYSTEMS, METHODS AND ARTICLES

(71) Applicant: View Point Medical, Inc., Carlsbad, CA (US)

(72) Inventor: William Blair, San Diego, CA (US)

(73) Assignee: VIEW POINT MEDICAL, INC., Carlsbad, CA (US)

(*) Notice: Subject to any disclaimer, the term of this patent is extended or adjusted under 35 U.S.C. 154(b) by 80 days.

(21) Appl. No.: 17/003,478

(22) Filed: Aug. 26, 2020

(65) Prior Publication Data

US 2021/0077076 A1  Mar. 18, 2021

Related U.S. Application Data

(60) Provisional application No. 62/892,952, filed on Aug. 28, 2019.

(51) Int. Cl.
*A61B 8/08* (2006.01)
*A61B 90/00* (2016.01)
*A61B 8/00* (2006.01)

(52) U.S. Cl.
CPC ............ *A61B 8/5246* (2013.01); *A61B 8/488* (2013.01); *A61B 8/5269* (2013.01); *A61B 8/54* (2013.01);
(Continued)

(58) Field of Classification Search
CPC ..... A61B 8/5246; A61B 8/488; A61B 8/5269; A61B 8/54; A61B 90/39; A61B 2090/3925
See application file for complete search history.

(56) References Cited

U.S. PATENT DOCUMENTS 5,512,094 A   4/1996 Linton
6,161,034 A   12/2000 Burbank et al.
(Continued)

FOREIGN PATENT DOCUMENTS

CN   102389576 A   3/2012
CN   103803556 A   5/2014
(Continued)

OTHER PUBLICATIONS

Kamaya et al., Twinkling artifact on color Doppler sonography: dependence on machine parameters and underlying cause, AJR Am J Roentgenol. Jan. 2003;180(1):215-22. doi: 10.2214/ajr.180.1. 1800215. (Year: 2003).*

(Continued)

*Primary Examiner* — Amelie R Davis
*Assistant Examiner* — John Denny Li
(74) *Attorney, Agent, or Firm* — Cozen O'Connor

(57) ABSTRACT

Markers for use in bodily tissue take a variety of forms, and may include a plurality of ultrasound reflective elements, for example hollow shells filled with air, and a hydrogel that binds the ultrasound reflective elements. The hydrogel may be natural or artificial and may be cross-linked. An ultrasound system advantageously injects variance in a drive signal, that varies a frequency or phase of an ultrasound interrogation signal from a nominal frequency or nominal phase. The amount of variation is preferable one to six orders of magnitude less than the nominal frequency or phase. The ultrasound system can present or detect a twinkling artifact at least in a Doppler mode of operation, resulting from interaction of the varying interrogation signal with the ultrasound reflective elements.

26 Claims, 10 Drawing Sheets

(52) U.S. Cl.
CPC ...... *A61B 90/39* (2016.02); *A61B 2090/3925* (2016.02)

(56) References Cited

U.S. PATENT DOCUMENTS

| | | | |
|---|---|---|---|
| 6,221,326 B1 | 4/2001 | Amiche |
| 6,235,801 B1 | 5/2001 | Morales et al. |
| 6,331,166 B1 | 12/2001 | Burbank et al. |
| 6,347,241 B2 | 2/2002 | Burbank et al. |
| 6,427,081 B1 | 7/2002 | Burbank et al. |
| 6,494,841 B1 | 12/2002 | Thomas et al. |
| 6,567,689 B2 | 5/2003 | Burbank et al. |
| 6,699,206 B2 | 3/2004 | Burbank et al. |
| 6,725,083 B1 | 4/2004 | Burbank et al. |
| 6,862,470 B2 | 3/2005 | Burbank et al. |
| 6,996,433 B2 | 2/2006 | Burbank et al. |
| 7,322,938 B2 | 1/2008 | Burbank et al. |
| 7,322,939 B2 | 1/2008 | Burbank et al. |
| 7,322,940 B2 | 1/2008 | Burbank et al. |
| 7,651,505 B2 | 1/2010 | Lubock et al. |
| 7,792,569 B2 | 9/2010 | Burbank et al. |
| 7,871,438 B2 | 1/2011 | Corbitt |
| 7,970,454 B2 | 6/2011 | Jones et al. |
| 7,983,734 B2 | 7/2011 | Jones et al. |
| 8,157,862 B2 | 4/2012 | Corbitt |
| 8,177,792 B2 | 5/2012 | Lubock et al. |
| 8,219,182 B2 | 7/2012 | Burbank et al. |
| 8,224,424 B2 | 7/2012 | Burbank et al. |
| 8,361,082 B2 | 1/2013 | Jones et al. |
| 8,440,229 B2 | 5/2013 | Trogler et al. |
| 8,498,693 B2 | 7/2013 | Jones et al. |
| 8,626,269 B2 | 1/2014 | Jones et al. |
| 8,626,270 B2 | 1/2014 | Burbank et al. |
| 8,668,737 B2 | 3/2014 | Corbitt |
| 8,680,498 B2 | 3/2014 | Corbitt et al. |
| 8,718,745 B2 | 5/2014 | Burbank et al. |
| 8,784,433 B2 | 7/2014 | Lubock et al. |
| 8,880,154 B2 | 11/2014 | Jones et al. |
| 9,044,162 B2 | 6/2015 | Jones et al. |
| 9,149,341 B2 | 10/2015 | Jones et al. |
| 9,220,585 B2 | 12/2015 | Horton et al. |
| 9,327,061 B2 | 5/2016 | Govil et al. |
| 9,480,554 B2 | 11/2016 | Corbitt |
| 9,579,077 B2 | 2/2017 | Casanova et al. |
| 9,743,909 B1* | 8/2017 | Sapozhnikov ........... A61N 7/02 |
| 9,801,688 B2 | 10/2017 | Jones et al. |
| 9,820,824 B2 | 11/2017 | Jones et al. |
| 9,861,294 B2 | 1/2018 | Jones et al. |
| 10,172,674 B2 | 1/2019 | Jones et al. |
| 2004/0116806 A1 | 6/2004 | Burbank et al. |
| 2004/0187524 A1 | 9/2004 | Sen et al. |
| 2004/0236213 A1 | 11/2004 | Jones et al. |
| 2005/0008578 A1 | 1/2005 | Schmidt |
| 2005/0158390 A1 | 7/2005 | Rana et al. |
| 2006/0293581 A1 | 12/2006 | Plewes et al. |
| 2007/0276252 A1 | 11/2007 | Kolasa et al. |
| 2008/0097207 A1 | 4/2008 | Cai |
| 2011/0196285 A1 | 8/2011 | Chen et al. |
| 2011/0229576 A1 | 9/2011 | Trogler et al. |
| 2012/0052012 A1 | 3/2012 | Chenite et al. |
| 2013/0039848 A1 | 2/2013 | Bradbury et al. |
| 2013/0066195 A1 | 3/2013 | Sirimanne et al. |
| 2013/0230570 A1 | 9/2013 | Trogler et al. |
| 2014/0017130 A1 | 1/2014 | Trogler et al. |
| 2014/0243675 A1 | 8/2014 | Burbank et al. |
| 2015/0057546 A1 | 2/2015 | Yoon et al. |
| 2015/0143688 A1 | 5/2015 | Garbini et al. |
| 2015/0173848 A1 | 6/2015 | Bolan et al. |
| 2015/0273061 A1 | 10/2015 | Trogler et al. |
| 2016/0143624 A1 | 5/2016 | Liberman et al. |
| 2016/0346404 A1 | 12/2016 | Trogler et al. |
| 2017/0066162 A9 | 3/2017 | Fisher |
| 2017/0209601 A1 | 7/2017 | Kumar et al. |
| 2018/0021102 A1 | 1/2018 | Azizian et al. |
| 2018/0065859 A1 | 3/2018 | Kummel et al. |
| 2018/0092987 A1 | 4/2018 | Trogler et al. |
| 2018/0280111 A1* | 10/2018 | Parish ................... A61B 90/39 |
| 2018/0289444 A1 | 10/2018 | Blair et al. |
| 2019/0176372 A1 | 6/2019 | Fisher et al. |
| 2019/0192253 A1 | 6/2019 | Yang et al. |
| 2019/0365345 A1* | 12/2019 | Byram ................... A61B 8/469 |

FOREIGN PATENT DOCUMENTS

| | | | |
|---|---|---|---|
| CN | 105377243 A | 3/2016 |
| JP | 2013536024 A | 9/2013 |
| JP | 2016505475 A | 2/2016 |
| JP | 2016516729 A | 6/2016 |
| JP | 6898603 B2 | 6/2021 |
| KR | 20150063097 A | 6/2015 |
| WO | 2006105353 A2 | 10/2006 |
| WO | 2009023697 A2 | 2/2009 |
| WO | 2012142625 A2 | 10/2012 |
| WO | 2014052911 A1 | 4/2014 |
| WO | 2016149711 A1 | 9/2016 |
| WO | 2018097891 A1 | 5/2018 |
| WO | 2018187594 A2 | 10/2018 |
| WO | 2019067441 A1 | 4/2019 |

OTHER PUBLICATIONS

Gorsd, Marina N. et al., "Synthesis and characterization of hollow silica spheres", Procedia Material Science, 2015, vol. 8, pp. 567-576.

International Preliminary Report on Patentability dated: Feb. 16, 2010 in International Application No. PCT/US2008/072972 filed: Aug. 13, 2008 and published as: WO 2009/023697 on Feb. 19, 2009, 7 pages.

International Preliminary Report on Patentability dated: Mar. 1, 2016 in International Application No. PCT/US2014/052911 filed: Aug. 27, 2014 and published as: WO 2015/031482 on Mar. 1, 2015, 9 pages.

International Preliminary Report on Patentability dated: Sep. 19, 2017 in International Application No. PCT/US2016/023492 filed: Mar. 21, 2016 and published as: WO 2016/149711 on Sep. 22, 2016, 6 pages.

International Search Report and Written Opinion dated: Aug. 16, 2016 in International Application No. PCT/US2016/023492 filed: Mar. 21, 2016 and published as: WO 2016/149711 on Sep. 22, 2016, 9 pages.

International Search Report and Written Opinion dated: Dec. 3, 2018 in International Application No. PCT/US2018/026291, 14 pages.

International Search Report and Written Opinion dated: Feb. 19, 2009 in International Application No. PCT/US2008/072972 filed: Aug. 13, 2008 and published as: WO 2009/023697 on Feb. 19, 2009, 9 pages.

International Search Report and Written Opinion dated: Oct. 3, 2015 in International Application No. PCT/US2014/052911 filed: Aug. 27, 2014 and published as: WO 2015/031482 on Mar. 5, 2015, 14 pages.

Arnal, Pablo M, et al., "High-temperature-stable catalysts by hollow sphere encapsulation," Angew Chern Int Ed Engl. Dec. 4, 2006;45(48):8224-7.

Brinker, C.J., "Hydrolysis and Condensation of Silicates: Effects on Structure", Journal of Non-Crystalline Solids, vol. 100, 1988, pp. 31-50.

Bunker, Christopher E, et al., "Low-Temperature Stability and High-Temperature Reactivity of Iron-Based Core-Shell Nanoparticles", J. Am Chem. Soc., 2004, vol. 126, No. 35, pp. 10852-10853.

Caruntu, Daniela, et al., "Synthesis of Variable-Sized Nanocrystals of Fe3O4 with High Surface Reactivity." Chemistry of Materials, vol. 16(25), pp. 5527-5534. (Year: 2004).

Caruso, Frank, et al., "Electrostatic Self-Assembly of Silica Nanoparticle-Polyelectrolyte Multilayers on Polystyrene Latex Particles," J. Am Chem. Soc., 1998, 120 (33), pp. 8523-8524.

Caruso, Frank, et al., "Magnetic Nanocomposite Particles and Hollow Spheres constructed by a Sequential Layering Approach." Chemistry of Materials, vol. 13, pp. 109-116. (Year: 2001).

(56) References Cited

OTHER PUBLICATIONS

Caruso, Frank, et al., "Nanoengineering of Inorganic and Hybrid Hollow Spheres by Colloidal Templating," Science Nov. 6, 1998: vol. 282, Issue 5391, pp. 1111-1114.
Cha, Jennifer N, et al., "Biomimetic synthesis of ordered silica structures mediated by block copolypeptides", Nature, vol. 403, Issue 6767, pp. 289-292 (2000).
Chang, Song-Yuan , et al., "Preparation and Properties of Tailored Morphology, Monodisperse Colloidal Silica-Cadmium Sulfide Nanocomposites,", J Am. Chem. Soc., Jul. 1994, 116 (15), pp. 6739-6744.
Cornelissen, Jeroen J.L.M, et al., "Versatile synthesis of nanometer sized hollow silica spheres," Chem. Commun., 2003,8, 1010-1011.
Ding, Xuefeng , et al., "A novel approach to the synthesis of hollow silica nanoparticles," Materials Letters 2004, 58(27-28), 3618-3621.
Huang, Chih-Chia, et al., "Shell-by-shell synthesis of multi-shelled mesoporous silica nanospheres for optical maging and drug delivery", Biomaterials, 32, 556-564,. (Year: 2011).
Jin, Pu, et al., "Synthesis and catalytic properties of nickel-silica composite hollow nanospheres" J Phys Chem B. May 1, 2004;108(20):6311-4. doi: 10.1021/jp049754g.
Kato, Noritaka , et al., "Synthesis of monodisperse mesoporous silica hollow microcapsules and their release of loaded materials." Langmuir. Sep. 7, 2010;26(17):14334-44. doi: 10.1021/la1024636.
Kempen, Paul J, et al., "Theranostic Mesoporous Silica Nanoparticles Biodegrade after Pro-Survival Drug Delivery and Ultrasound/Magnetic Resonance Imaging of Stem Cells." Theranostics 2015: 5(6) 631-642.
Lee, Jeongwoo, et al., "Synthesis of polystyrene/silica composite particles by soap-free emulsion polymerization using positively charged colloidal silica." J Colloid Interface Sci. Jun. 2007 A181;310(1):112-20. Epub Feb. 15, 2007.
Liberman, Alexander, et al., "Color Doppler Ultrasound and gamma imaging of intratumorally injected 500nm iron-silica nanoshells" ACS Nano, Jul. 23, 2013, 7(7) 6367-6377.
Liberman, Alexander , et al., "Hollow iron-silica nanoshells for enhanced high intensity focused ultrasound" J Surg Res, May 10, 2014, 190(2): 391-398.
Liberman, Alexander, et al., "Mechanically tunable hollow silica ultrathin nanoshells for ultrasound contrast agents" Adv Funct Mater, 25(26) 4049-4057, May 21, 2015.
Liu, Jian, et al., "From Hollow Nanosphere to Hollow Microsphere: Mild Buffer Provides Easy Access to Tunable Silica Structure," J. Phys. Chem. C 2008, 112(42), pp. 16445-16451.
Lu, Yu, et al., "Synthesis and crystallization of hybrid spherical colloids composed of polystyrene cores and silica shells," Langmuir, American Chemical Society, 2004, pp. 3464-3470, vol. 20, No. 8.
Mallery, Susan R, "Formulation and In-Vitro and In-Vivo Evaluation of a Mucoadhesive Gel Containing Freeze Dried Black Raspberries: Implications for Oral Cancer Chemoprevention", Pharma Res. 24(4), 728-737 (Year: 2007).
Martinez, Paul H, et al., Martinez et al., "Hard shell gas-filled contrast enhancement particles for colour Doppler ultrasound imaging of tumors" Medchemcomm, Oct. 1, 2010(4) 266-270.
Mori, Hideharu, et al., "Organic-Inorganic Nanoassembly Based on Complexation of Cationic Silica Nanoparticles and Weak Anionic Polyelectrolytes in Aqueous and Alcohol Media," Langmuir, vol. 20(5), 2004, pp. 1934-1944.
Nandiyanto, Asep Bayu Dani, et al., "Mesopore-Free Hollow Silica Particles with Controllable Diameter and Shell Thickness Via Additive-Free Synthesis." Langmuir. Jun. 12, 2012;28(23):8616-24. doi: 10.1021/la301457v. Epub May 31, 2012.
Paefgen, Vera, "Evolution of contrast agents for ultrasound imaging and ultrasound-mediated drug delivery," Front Pharmacol 2015, 6, 197, 16 pages.
Parida, Sudam K, et al., "Adsorption of organic molecules on silica surface," Advances in Colloid and Interface Science, 2006, vol. 121, Issue: 1-3, pp. 77-110.

Slowing, Igor I, et al., . "Mesoporous Silica Nanoparticles for Drug Delivery and Biosensing Applications," Adv. Funct Mater, vol. 17, Issue Apr. 8, 2007 pp. 1225-1236.
Su, Yang, et al., "Synthesis of hierarchical hollow silica microspheres containing surface nanoparticles employing the quasi-hard template of poly(4-vinylpyridine) microspheres." Langmuir. Jul. 19, 2011;27 (14):8983-9. doi: 10.1021/la2014573. Epub Jun. 23, 2011.
Ta, Casey N., et al., "Integrated processing of contrast pulse sequencing ultrasound maging for enhanced active contrast of hollow gas filled silica nanoshells and microshells," J. Vac. Sci. Technol. B 30(2), Mar./Apr. 2012, 6 pages.
Tada, Dayane B, et al., "Methylene Blue-Containing Silica-Coated Magnetic Particles: A Potential Magnetic Carrier tor Photodynamic Therapy", Langmuir, 23, 8194-8199. (Year: 2007).
Tissot, Isabelle, et al., "Hybrid Latex Particles Coated with Silica," Macromolecules, Jun. 7, 2001, 34 (17), pp. 5737-5739.
Van Bommel, Kjeld J.C, et al., "Poly(L-lysine) Aggregates as Templates for the Formation of Hollow Silica Spheres," Adv. Mater. vol. 13, Issue 19, Oct. 2001, pp. 1472-1476.
Velikov, Krassimir P, et al., "Synthesis and Characterization of Monodisperse Core-Shell Colloidal Spheres of Zinc Sulfide and Silica," Langmuir, Jul. 10, 2001, 17 (16), pp. 4779-4786.
Voss, R.K., "Doppler Ultrasound-Visible Signal Mark Microspheres are Better Identified than HydroMARK® Clips in a Simulated Intraoperative Setting in Breast and Lung Cancer," Presented at Society of Surgical Oncology meeting Chicago Illinois, Mar. 21-24, 2018.
Wang, H., "Spherical silicon-shell photonic band gap structures fabricated by laser-assisted chemical vapor Teposition," J. Appl. Phys. 2007, 101, 033129, Published Online: Feb. 15, 2007 Accepted: Dec. 2006.
Ward, Erin, et al., "Utilization of Iron (III) Doped Nanoshells for in vivo Marking of Non-palpable Tumors using VX2 Rabbit Model" Am. J. Surg., Dec. 2016, 212(6): 1140-1146.
Wu, Dazhen , et al., "Novel One-Step Route for Synthesizing CdS/Polystyrene Nanocomposite Hollow Spheres," Langmuir May 26, 2004, 20, (13), pp. 5192-5195.
Wu, W., et al., "Synthesis of magnetic hollow silica using polystyrene bead as a template." Journal of Magnetism and Magnetic Materials, vol. 311(2), pp. 578-582, available online Sep. 22, 2006.
Xu, Xiangling , et al., "Synthesis and utilization of monodisperse hollow polymeric particles in photonic crystals" J Am Chem Soc. Jun. 4, 2004;126(25):7940-5.
Yao, Hiroshi, et al., "Electrolyte Effects on CdS Nanocrystal Formation in Chelate Polymer Particles: Optical and Distribution Properties", Langmuir 1998, 14(3), 595-601.
Yildirim, Adem, et al., "Stable Encapsulation of Air in Mesoporous Silica Nanoparticles: Fluorocarbon-Free Nanoscale Ultrasound Contrast Agents," Adv Healthc Mater. Jun. 2016; 5(11): 1290-1298.
Zhang, Kun, et al., "Double-scattering/reflection in a Single Nanoparticle for intensified Ultrasound Imaging," Sci Rep, 2015 5:8766.
Zhong, Ziyi, et al., "Preparation of mesoscale hollow spheres of TiO2 and SnO2 by templating against crystalline arrays of polystyrene beads," Adv. Mater. 2000,12(3), 206-209.
Zhou, W., et al., "Drug-loaded, magnetic, hollow silica nanocomposites for nanomedicine." Nanomedicine Nanotechnology, Biology and Medicine, vol. 1(3), 2005, pp. 233-237.
Zhou, Dejian, et al., "Influence of the Foundation Layer on the Layer-by-Layer Assembly of Poly-L-lysine and Poly (styrenesulfonate) and Its Usage in the Fabrication of 3D Microscale Features." Langmuir, vol. 20(21), 2004, pp. 9089-9094.
Zhu, Yufang, et al., "Stimuli-responsive controlled drug release from a hollow mesoporous silica sphere/polyelectrolyte multilayer core-shell structure," Angew Chem Int Ed Engl. Aug. 12, 2005;44(32):5083-7.
European Search Report issued in European Application No. 18781390. 2, dated Jan. 19, 2021, 8 pages.
International Search Report & Written Opinion issued in Application No. PCT/US2020/048023, dated Dec. 9, 2020, 17 pages.
International Search Report and Written Opinion, dated Apr. 6, 2021, in International Application No. PCT/US/2020/062322, 20 pages.

(56) References Cited

OTHER PUBLICATIONS

International Search Report and Written Opinion, dated Mar. 24, 2021, in International Application No. PCT/US2020/062272, 12 pages.
Office Action issued in Japanese Patent Application No. 2019-555229, dated Dec. 24, 2020, 8 pages.
Li, Xin, et al., "Formation of Gold Nanostar-Coated Hollow Mesoporous Silica for Tumor Multimodality Imaging and Photothermal Therapy", 5817-5827.
Mitchell, et al., "Iron(III)-Doped, Silica Nanoshelis: A Biodegradable Form of Silica" J. Am. Chem. Soc. 2012, 34, 13997-14003 (Year: 2021).
First Office Action dated Nov. 9, 2021 for CN201880023936.2, with translation, 24 pages.
Hu et al., "Facile synthesis of amino-functionalized hollow silica microspheres and their potential application for ultrasound imaging, He Hu et al.," Journal of Colloid and Interface Science, vol. 358, pp. 392-398, 2011.
Lu et al., "Synthesis of hollow silica microspheres and their applications in ultrasound imaging", Journal of Shanghai Normal University, vol. 41, Issue 4, pp. 432-439, 2012.
Notice of Reasons for Rejection, issued in corresponding Japanese Application No. 2021-063419, dated Apr. 11, 2022, 4 pages (English Translation).

* cited by examiner

ULTRASOUND MARKER DETECTION, MARKERS AND ASSOCIATED SYSTEMS, METHODS AND ARTICLES

BACKGROUND

Field

This disclosure generally relates to ultrasound detection of markers in bodily tissue, and further relates to markers, and associated systems, method articles of manufacture, and/or kits, which may, for example, facilitate detection of margins of bodily tissue (e.g., abnormal bodily tissue) to be monitored, biopsied, excised or ablated.

Description of the Related Art

Various types of markers are used to mark bodily tissue that is to be monitored over time, or biopsied, excised or ablated. Some markers may, for example, allow or enhance visual detection by a surgeon. Some markers allow detection via various energy emitted imaging modalities, for example ultrasound imaging, radiological imaging such as X-ray imaging or magnetic resonance imaging (MRI). These different imaging modalities are often employed in different scenarios, and markers detectable under the various visual detecting or imaging modalities typically require different physical characteristics in order to be detectable.

Some markers may be permanent, while other markers may be absorbable by the body over a period of time. For example, it may be useful to mark a portion of bodily tissue for subsequent evaluation or detection over a fairly extended period (e.g., months, year).

There is a need for markers which are detectable via ultrasound, as well as additional imaging modalities, and which are optionally absorbable over time.

There is also a need for improved imaging techniques that do not employ ionizing radiation, for instance improved ultrasound imaging techniques that may enhance detection of markers in bodily tissue and/or detection of the margins of certain bodily tissues (e.g., abnormal bodily tissues, for instance tumors, or bodily tissues suspected of being abnormal).

BRIEF SUMMARY

This disclosure generally relates to ultrasound detection of markers in bodily tissue, and further relates to detectable markers, and associated systems, method, articles of manufacture, and/or kits which may, for example, facilitate more precise detection of tissue to be monitored, biopsied, excised or ablated than otherwise possible using conventional approaches.

Markers for use in bodily tissue take a variety of forms, and may include a plurality of ultrasound reflective elements and a hydrogel that binds the ultrasound reflective elements. The ultrasound reflective elements may, for example, take the form of hollow shells. Cavities of the hollow shells may be filled with a fluid, for example a gas such air, a liquid, or a combination of gas and liquid (e.g., a vapor) and may advantageously be devoid of perfluorocarbon. The hollow shells may be porous, and may be coated with a hydrophobic coating to at least temporally seal the pores to prevent or delay the release of fluid (e.g., gas) from the cavities to an exterior of the hollow shells. The ultrasound reflective elements may comprise or consist of silica in one or more forms. The hydrogel may be a natural, for instance gelatin, or an artificial hydrogel, for instance polyethylene glycol (PEG). The hydrogel may be partially or fully cross-linked. The hydrogel may be engineered to be absorbed by the body over a period of time, or alternatively may be non-absorbable.

An ultrasound system advantageously injects variance in a drive signal, that varies a frequency or phase of an ultrasound interrogation signal from a nominal frequency or nominal phase. The amount of variation is preferable one to six orders of magnitude less than the nominal frequency or phase. The variance may be periodic, may form of follow a defined pattern, or may be pseudo-random or random. The ultrasound system can present or detect a twinkling artifact at least in a Doppler mode of operation, resulting from interaction of the varying interrogation signal with the ultrasound reflective elements.

The markers and the ultrasound system may be provided as a kit, the hollow shell ultrasound reflective elements being particular effective at producing a twinkling artifact when subjected to an ultrasound interrogation signal with a variance in frequency or phase, preferably in a range of one to six orders of magnitude less than a nominal frequency or phase, during Doppler mode operation.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with microcontrollers, piezo-electric devices or transducers, power supplies such as DC/DC converters, wireless radios (i.e., transmitters, receivers or transceivers), computing systems including client and server computing systems, and networks (e.g., cellular, packet switched), as well as other communications channels, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

In particular, described herein are new tissue markers and ultrasound techniques, systems, methods, and articles of manufacture to advantageously mark tissue for later evaluation, excision, and/or ablation. Such may, for example, be used to more precisely define the margins of abnormal or suspect tissue (e.g., a tumor) in bodily tissue.

Figure 1:
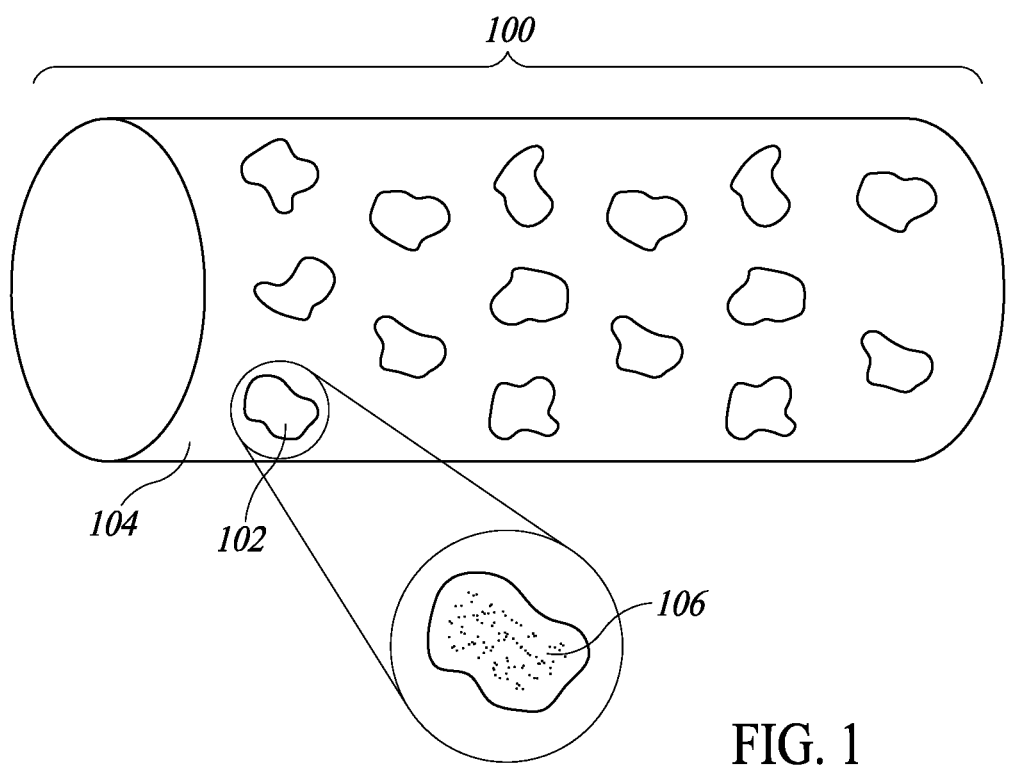
FIG. 1 is an isometric view of a marker to mark bodily tissue according to one illustrated implementation, the marker comprising a plurality of ultrasound reflective elements and a hydrogel carrier, with an enlarged view showing one of the ultrasound reflective elements in detail including a contrast agent carried by the ultrasound reflective element to enhance detection for in other imaging modalities.

FIG. 1 shows a marker 100 to mark bodily tissue, according to at least one illustrated implementation.

In at least one implementation, the marker 100 comprises a plurality of ultrasound reflective elements 102 (only one called out) carried by the hydrogel carrier 104. The hydrogel carrier 104 binds the plurality of ultrasound reflective elements 102 together.

The hydrogel carrier 104 may take variety of forms. The hydrogel carrier 104 may comprise a natural hydrogel, for example a gelatin. The hydrogel carrier 104 may comprise an artificial hydrogel, for example a polyvinyl alcohol (PVA)

hydrogel or a polyethylene glycol (PEG) hydrogel. The hydrogel carrier 104 may comprise a combination of a natural hydrogel (e.g., gelatin) and an artificial hydrogel (e.g., PVA hydrogel, PEG hydrogel).

In at least some of the implementations, the hydrogel carrier 104 is an at least partially cross-linked hydrogel. In at least some of the implementations, the hydrogel carrier 104 is a gelatin, for example a cross-linked gelatin. In at least some of the implementations, the hydrogel carrier 104 is a PVA hydrogel, for example a cross-linked PVA hydrogel. In at least some of the implementations, the hydrogel carrier 104 is a PEG hydrogel, for example a cross-linked PEG hydrogel. In at least some of the implementations, the hydrogel carrier 104 comprises a combination of a natural hydrogel and an artificial hydrogel, for instance as respective gel bodies coupled to one another.

The hydrogel carrier 104 may be non-absorbable by the body (e.g., persistent over 60 years or longer), or may be absorbable by the body within of a period of time. Where absorbable, the hydrogel carrier 104 may be engineered (e.g., via extent or strength of cross-linking) to persist in the body for a period of time, for example being persistent over a period of hours, days, a week or weeks, a month or months, or even for a year or years. In at least some implementations, outer or exposed portions of an absorbable hydrogel carrier 104 when implanted may absorb sooner than more interior portions of the hydrogel carrier, the absorption occurring as various portions of the hydrogel carrier 104 are exposed to bodily tissue, including bodily fluids. In at least some implementations, the hydrogel carrier 104 can be engineered (e.g., controlled cross-linking profiles) to cause some portions to absorb faster than other portions and/or to ensure that some portions persist longer than other portions. Thus, various absorption profiles may be formed across or through a hydrogel carrier.

Each ultrasound reflective element is highly reflective of ultrasound. Each ultrasound reflective element preferably has in irregular surface, for example having a rough outer surface to cause scattering or dispersion of ultrasound energy. The ultrasound reflective elements 102 may be in the nanometer size range (e.g., 1.8 microns to about 2.2 microns).

The ultrasound reflective elements 102 may take any of a large variety of forms.

In at least one implementation, each ultrasound reflective element comprises a particle that is not a hollow shell, but which is a solid particle or alternatively a porous non-spherical particle. Each ultrasound reflective element may, for example, comprise a respective particle that comprises, or consists of, silica without a hollow interior cavity. Each particle may comprise one or more layers (not shown in FIG. 1). The one or more layers may including contrast agents 106, to enhance detection via modalities other than ultrasound imaging, as discussed below. Alternatively, one or more ultrasound reflective elements may comprise, or consist of, one or more contrast agents.

Contrast agents 106 may, for example include one or more contrast agents that enhance visual detection, or detection using X-ray or MRI imaging modalities. For example, some or all of the ultrasound reflective elements 102 may include a dye to enhance detection by direct visual observation. The dye may advantageously be a florescent dye. The dye may, for example, comprise or consist of methylene blue. Also for example, some or all of the ultrasound reflective elements 102 may include or consist of a radiopaque material (e.g., gold, platinum, tantalum, bismuth, barium and the like). Also for example, some or all of the ultrasound reflective elements 102 may include or consist of an MRI imaging material (e.g., as gadolinium including compounds such as gadolinium DTPA, ferrous gluconate, ferrous sulfate and the like).

Alternatively, one or more contrast agents 106, for example the contrast agents 106 identified above or a wire (e.g., helical wound metal wire) or other radiopaque element such as a radiopaque clip, may be incorporated into or about the hydrogel carrier 104, in addition to the ultrasound reflective elements 102.

In at least one implementation, each ultrasound reflective element 102 comprises a hollow shell. Each hollow shell has at least one outer wall that forms a cavity. In at least some implementations, the hollow shell is a multi-layer hollow shell, for example a shell with an inner layer and an outer layer. Each hollow shell is highly reflective of ultrasound. Each hollow shell preferably has in irregular surface, for example having a rough outer surface to cause scattering or dispersion of ultrasound energy. The hollow shells may be in the nanometer size range.

In at least some implementations, each hollow shell may comprise, or alternatively consist of, a silica or titanium dioxide. Some techniques to form hollow shells in the nanometer size range are described, for example in: U.S. patent application 60/955,678; U.S. patent application 61/034,468; U.S. patent application Ser. No. 12/673,224 (now U.S. Pat. No. 8,440,229); International patent application PCT/US2008/072972; U.S. patent application Ser. No. 13/866,940 (now U.S. Pat. No. 9,220,685); U.S. patent application Ser. No. 15/722,436; U.S. patent application 61/707,794; International patent application PCT/US2013/062436; U.S. patent application Ser. No. 15/706,446; U.S. patent application 62/135,653; U.S. patent application Ser. No. 15/559,764; International patent application PCT/US2016/23492; U.S. patent application 62/483,274; U.S. patent application 62/645,677; U.S. patent application Ser. No. 15/946,479; and International patent application PCT/US2018/26291.

The hollow shells, or one or more layers of the hollow shell may comprise one or more contrast agents, for example the contrast agents identified above to enhance visual, radiological or MRI detection.

In at least some implementations, the cavity of the at least one hollow shell contains a fluid, that is a gas, a liquid, or a combination or mixture of a gas and a liquid. The gas may take the form of one material while the liquid takes the form of another material, different from the material that forms the gas. Alternatively, the gas and liquid may be the same material, just in different phase states. The combination or mixture of gas and liquid may, for instance, take the form of a vapor, either in a quiescent state or when subjected to ultrasound at some threshold level of energy which causes heating. The cavity of the at least one hollow shell may, for example, contain air. Alternatively, the cavity of the at least one hollow shell may contain an inert gas (e.g., nitrogen, argon). The cavity is preferably devoid of any perfluorocarbon, for instance whether in either gaseous and/or liquid forms.

Each hollow shell may be porous. Where the hollow shell contains a fluid (i.e., gas, liquid, or combination or mix of gas and liquid), the marker 100 may optionally include comprise a coating, preferably a hydrophobic coating, that at least temporarily seals one or more pores thereof.

In some implementations, the hydrogel may be expandable, for example when implanted into bodily tissue. In some implementations the marker 100 may, in an unexpanded state, have a length of about 2 mm to about 40 mm and a transverse dimension of about 0.5 mm to about 2 mm. The marker may have a ratio of size expansion from a dried unexpanded state to a water saturated expanded state of about 1:1.5 to about 1:10. The marker 100 may have a ratio of size expansion from a dried unexpanded state to a water saturated expanded state of about 1:2 to about 1:3.

Figure 2:
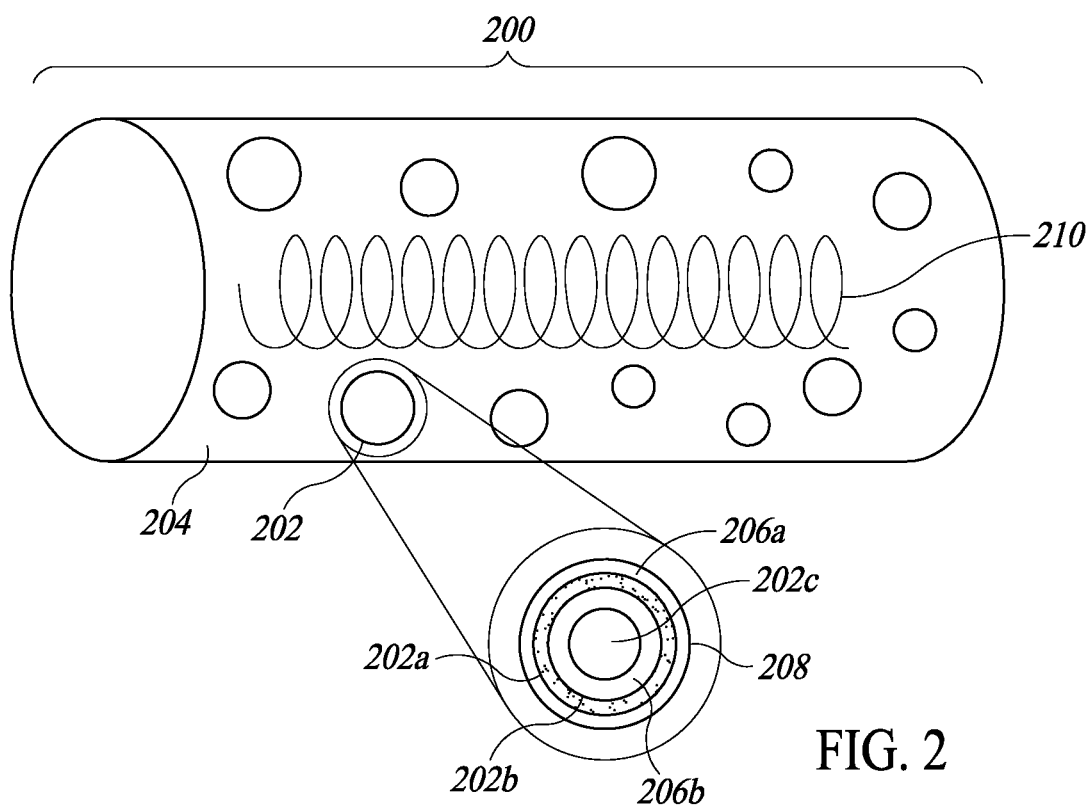
FIG. 2 is an isometric view of a marker to mark bodily tissue according to one illustrated implementation, the marker comprising a plurality of ultrasound reflective elements, a hydrogel, and an optional wire, with an enlarged view showing one of the ultrasound reflective elements in detail including contrast agents carried by the ultrasound reflective element to enhance detection for in other imaging modalities, as well as a hydrophobic coating.

FIG. 2 shows a marker 200 to mark bodily tissue, according to at least one illustrated implementation.

In at least one implementation, the marker 200 comprises at least one hollow shell 202, and preferably a plurality of hollow shells 202 (only one called out). Each hollow shell 202 has at least one outer wall that forms a cavity. In at least some implementations, the hollow shell 202 is a multi-layer hollow shell, for example a shell with an outer layer 202a, an inner layer 202b, and a cavity 202c. Each hollow shell 202 is highly reflective of ultrasound. Each hollow shell 202 preferably has in irregular surface, for example having a rough outer surface to cause scattering or dispersion of ultrasound energy. The hollow shells 202 may be in the nanometer size range (e.g., 1.8 microns to about 2.2 microns).

In at least some implementations, each hollow shell 202 may comprise, or alternatively consist of, a silica or titanium dioxide. Some techniques to form hollow shells 202 in the nanometer size range are described, for example in: U.S. patent application 60/955,678; U.S. patent application 61/034,468; U.S. patent application Ser. No. 12/673,224 (now U.S. Pat. No. 8,440,229); International patent application PCT/US2008/072972; U.S. patent application Ser. No. 13/866,940 (now U.S. Pat. No. 9,220,685); U.S. patent application Ser. No. 15/722,436; U.S. patent application 61/707,794; International patent application PCT/US2013/062436; U.S. patent application Ser. No. 15/706,446; U.S. patent application 62/135,653; U.S. patent application Ser. No. 15/559,764; International patent application PCT/US2016/23492; U.S. patent application 62/483,274; U.S. patent application 62/645,677; U.S. patent application Ser. No. 15/946,479; and International patent application PCT/US2018/26291 (published as WO 2018/187594.

In at least some implementations, the cavity 202c of the at least one hollow shell 202 contains a fluid, or a gas, or a combination or mixture of fluid(s) and gas(es). For example, the cavity 202c of the at least one hollow shell may contain air. Alternatively, the cavity 202c of the at least one hollow shell 202 may contain an inert gas (e.g., nitrogen, argon). The cavity 202c is preferably devoid of any perfluorocarbon, for instance whether in either gaseous and/or liquid forms.

Each hollow shell 202 may be porous. Where the hollow shell 202 contains a fluid (i.e., gas(es), liquid(s), or mix of gas(es) and liquid(s)), the marker 200 may optionally include comprise a coating, preferably a hydrophobic coating 208, that at least temporarily seals one or more pores thereof. The hydrophobic coating 208 may take the form of a hydrophobic polymer, for example a hydrophobic polymer that comprises octyltriethoxysilane.

One or more layers 202a, 202b of the hollow shell 202 may comprise one or more contrast agents 206a, 206b, to enhance detection via modalities other than ultrasound imaging, as discussed below.

Contrast agents may, for example include one or more contrast agents that enhance visual detection, or detection using X-ray or MRI imaging modalities. For example, some or all of the ultrasound reflective elements 102 may include a dye 206a (in outer most layer 202a) to enhance detection by direct visual observation. The dye may advantageously be a florescent dye. The dye may, for example, comprise or consist of methylene blue. Also for example, some or all of the ultrasound reflective elements 102 may include or consist of a radiopaque material (e.g., gold, platinum, tantalum, bismuth, barium and the like) and/or an MRI imaging material (e.g., as gadolinium including compounds such as gadolinium DTPA, ferrous gluconate, ferrous sulfate and the like) collectively 202b.

As noted above, the marker 200 may preferably comprise a plurality of hollow shells 202. The marker 200 may further comprise a hydrogel 204 that binds the plurality of hollow shells 202 together. In at least some of the implementations, the hydrogel 204 is an at least partially cross-linked hydrogel. In at least some of the implementations, the hydrogel 204 is a gelatin, for example a cross-linked gelatin. The hydrogel 204 may take variety of forms. For example, the hydrogel may be a natural hydrogel (e.g., gelatin) or an artificial hydrogel (e.g., polyvinyl alcohol (PVA) hydrogel, polyethylene glycol (PEG) hydrogel). The hydrogel 204 may be non-absorbable by the body (e.g., persistent over 60 years or longer), or may be absorbable by the body within of a period of time. Where absorbable, the hydrogel 204 may be engineered (e.g., via extent or strength of cross-linking) to persist in the body for a period of time, for example being persistent over a period of hours, days, a week or weeks, a month or months, or even for a year or years. In at least some implementations, outer or exposed portions of an absorbable hydrogel when implanted may absorb sooner than more interior portions of the hydrogel, the absorption occurring as various portions of the hydrogel are exposed to bodily tissue, including bodily fluids. In at least some implementations, the hydrogels 204 can be engineered (e.g., controlled cross-linking profiles) to cause some portions to absorb faster than other portions and/or to ensure that some portions persist longer than other portions. Thus, various absorption profiles may be formed across or through a hydrogel 204.

One or more contrast agents 206a, 206b, for example the contrast agents identified above or a radiopaque element (e.g., radiopaque wire, helical wound metal wire 210, radiopaque clip), may be incorporated into or about the hydrogel carrier, in addition to the hollow shells 202.

In some implementations, the hydrogel may be expandable, for example when implanted into bodily tissue. In some implementations the marker 200 may, in an unexpanded state, have a length of about 2 mm to about 40 mm and a transverse dimension of about 0.5 mm to about 2 mm. The marker may have a ratio of size expansion from a dried unexpanded state to a water saturated expanded state of about 1:1.5 to about 1:10. The marker 200 may have a ratio of size expansion from a dried unexpanded state to a water saturated expanded state of about 1:2 to about 1:3.

Figure 3:
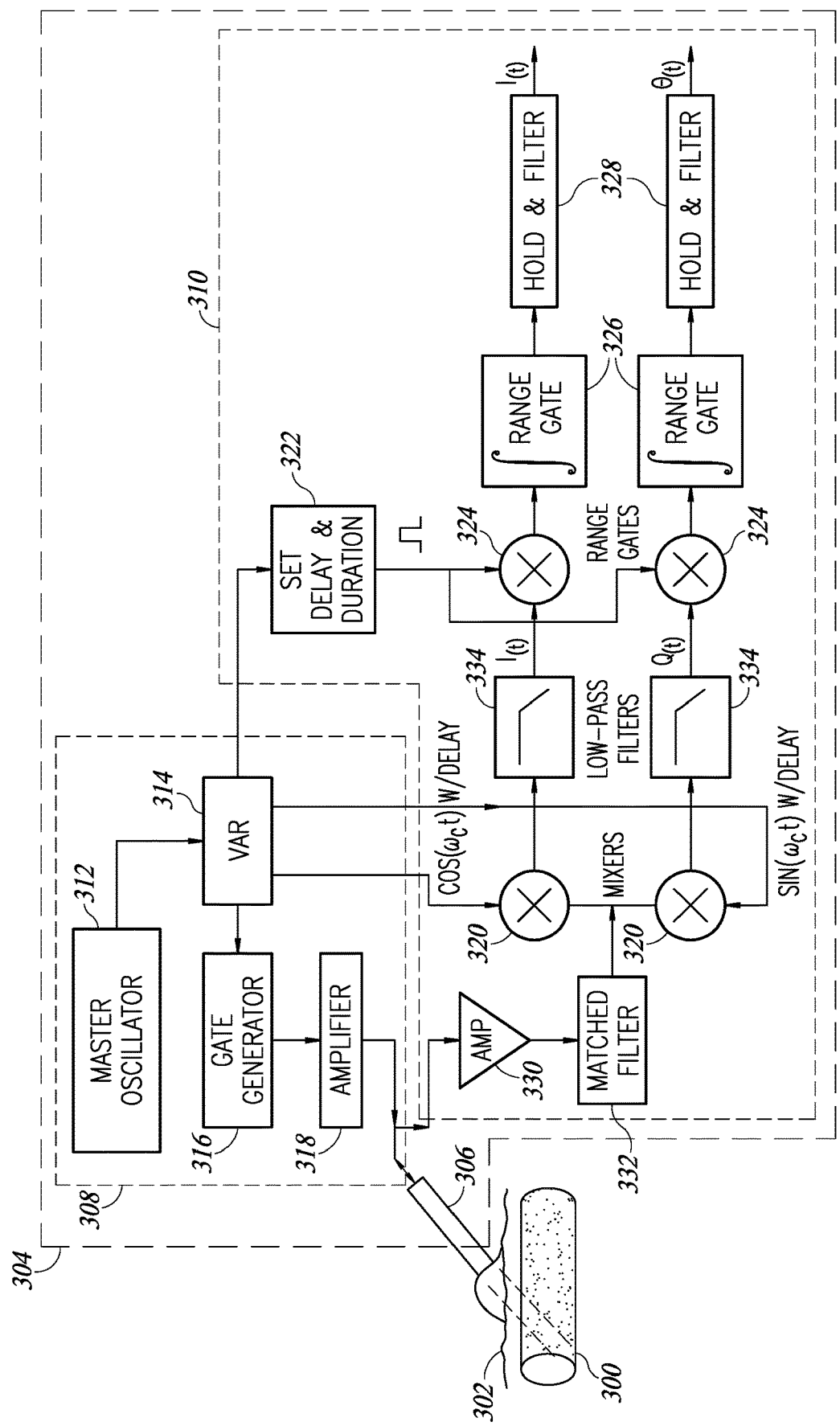
FIG. 3 is a schematic view of an analog pulse ultrasound imaging system according to at least one illustrated implementation, the analog pulse ultrasound imaging system which introduces a variation from a nominal pulse repetition frequency into a drive signal that drives an ultrasound transducer, and which is operable to detect, in a Doppler mode (e.g., color Doppler mode) of operation, a twinkling artifact in the received return signal, the twinkling artifact resulting from interaction of the ultrasound signal having the varied pulse repetition frequency with at least a portion of a marker that is ultrasound reflective and which preferably has an irregular surface.

FIG. 3 shows a marker 300 implanted in bodily tissue 302, and an analog pulse Doppler ultrasound system 304 including an ultrasound probe or transducer array 306 positioned to detect the marker 300, according to at least one illustrated embodiment.

The analog pulse Doppler ultrasound system 304 includes a transmit section 308 and a receive section 310. The transmit section 308 generates pulses and drives the ultrasound probe or transducer array 306 to emit ultrasound energy. The receive section 310 receives signals representative of the ultrasound energy returned from objects in the field of view of the ultrasound probe or transducer array 306, and processes the return signals based on one or more operational modes (e.g., A-mode, B-mode, M-mode, Doppler color mode, Doppler power mode). In some implementations, the analog pulse Doppler ultrasound system 304 will alternate between capturing B-mode frames and Doppler color or power mode frames, for example with the variation in the pulse repetition occurring during Doppler mode operation but not occurring during B-mode operation.

The analog pulse Doppler ultrasound system 304 includes a master clock or oscillator 312 which outputs a timing signal. The timing signal output by the master clock or oscillator 312 sets or is used to set a nominal pulse repetition frequency, that is the frequency at which ultrasound pulses repeat. In at least some implementations, the nominal pulse repetition frequency can be set by an operator, at least within some defined range. In other implementations, the nominal pulse repetition frequency may be a fixed characteristic of the particular analog pulse Doppler ultrasound system 304.

The transmit section 308 includes a variation circuit (VAR) 314 that introduces a variation in the clock signal provided by the master clock or oscillator 312, either directly or indirectly (e.g., via gate generator) introducing a variation from the nominal pulse repetition frequency into the drive signal used to drive the ultrasound probe or transducer array 306 during a Doppler mode operation. The variation may be a variation in time or a variation in phase, and the variation is a variation over a period of time. The variation may, for example, be implemented via one or more delay circuits or capacitors, which delay the clock signal. For example, a delay circuit may have an adjustable delay, or two or more different delay circuits, each with respective delays, may introduce delays of different durations to achieve the variation during the Doppler mode operation. The variation may be periodic, may follow a pattern, or may be pseudo-random, for instance produced via a pseudo-random number generator, also known as a random number generator (RNG). A periodic variation may have a period or frequency that is different from the nominal pulse repetition frequency. A periodic variation or variation that follows a pattern may be advantageously employed by the receive section 310. The variation may be introduced into the drive signal over a plurality of pulses emitted during a Doppler mode of operation during capture of one or more Doppler frames of ultrasound data to intentionally introduce an artifact that would typically be considered undesirable noise.

The variation is preferably at least one order of magnitude less than the nominal pulse repetition frequency, and more preferably two orders of magnitude, three orders of magnitude, four orders of magnitude, five orders of magnitude, or most preferably six orders of magnitude less than the nominal pulse repetition frequency.

The varied clock signal is supplied to a gate generator 316, which is communicatively coupled via an amplifier 318 to drive the ultrasound probe or transducer array 306. The varied clock signal is also supplied to the receive section 310, for example to a set of mixers 320, and a set delay and duration circuit 322. The set delay duration circuit 322 is communicatively coupled to a second set of mixers 324 of the receive section 310, which feed a set of range gates 326, which in turn feed a set of hold and filter circuits 328 of the receive section 310.

The receive section 310 receives signals representative of the ultrasound energy returned from objects in the field of view of the ultrasound probe or transducer array 306, and an amplifier 330 of the receive section 310 amplifies the return signals. A matched filter 332 filters the amplified return signals. The set of mixers 320 then mix in the varied clock signal, and the results are low pass filtered by a set of low pass filters 334 to provide for quadrature processing, via second set of mixers 324, range gates 326, and hold and filter circuits 328.

Figure 4:
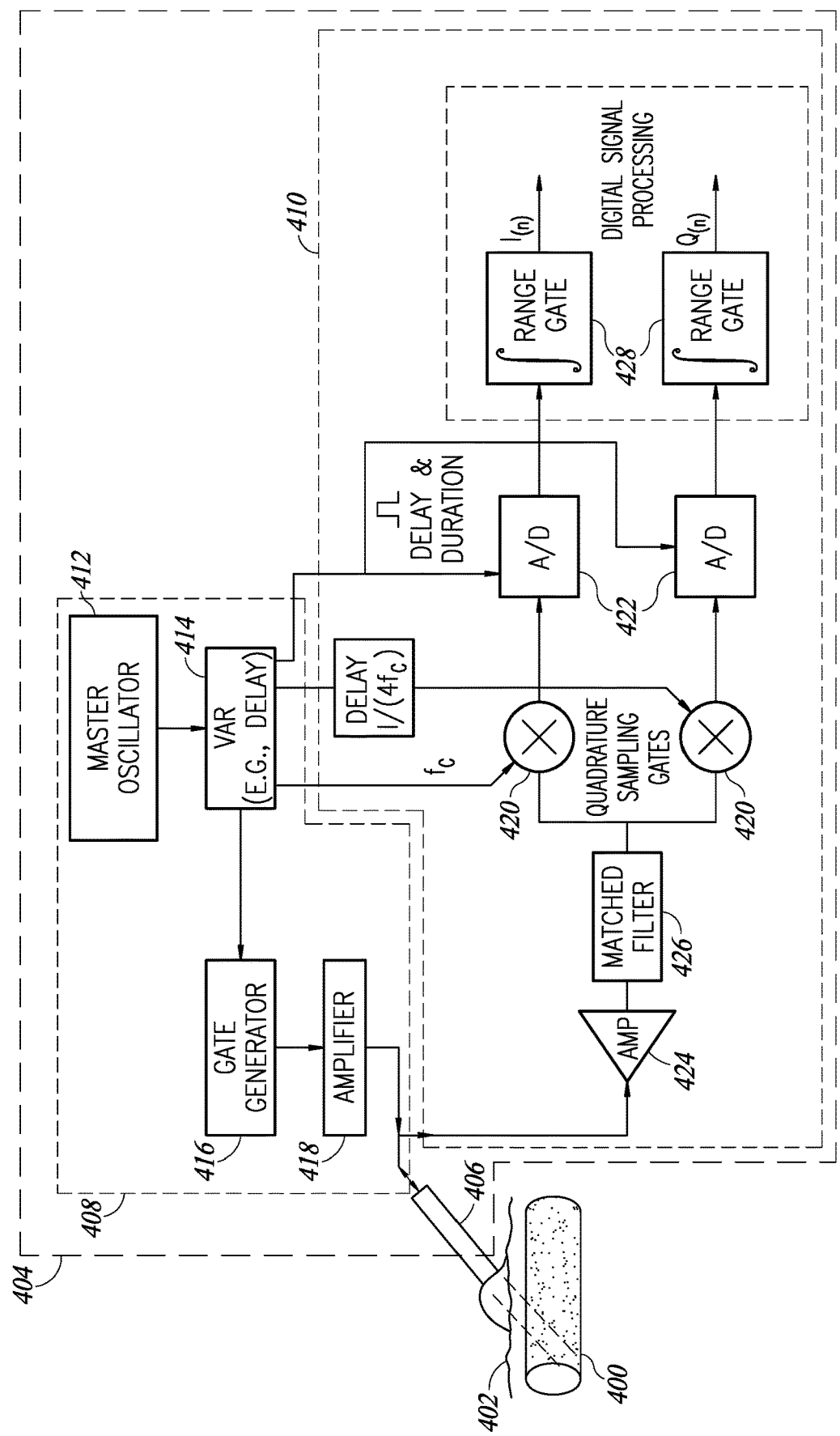
FIG. 4 is a schematic view of a digital pulse ultrasound imaging system according to at least one illustrated implementation, the digital pulse ultrasound imaging system which introduces a variation from a nominal pulse repetition frequency into a drive signal that drives an ultrasound transducer, and which is operable to detect, in a Doppler mode (e.g., color Doppler mode) of operation, a twinkling artifact in the received return signal, the twinkling artifact resulting from interaction of the ultrasound signal having the varied pulse repetition frequency with at least a portion of a marker that is ultrasound reflective and which preferably has an irregular surface.

FIG. 4 shows a marker 400 implanted in bodily tissue 402, and a digital pulse Doppler ultrasound system 404 include an ultrasound probe 406 positioned to detect the marker 400, according to at least one illustrated implementation.

The digital pulse Doppler ultrasound system 404 includes a transmit section 408 and a receive section 410. The transmit section 408 generates pulses and drives the ultrasound probe or transducer array 406 to emit ultrasound energy. The receive section 410 receives signals representative of the ultrasound energy returned from objects in the field of view of the ultrasound probe or transducer array 406, and processes the return signals based on one or more operational modes (e.g., A-mode, B-mode, M-mode, Doppler color mode, Doppler power mode). In some implementations, the digital pulse Doppler ultrasound system 404 will alternate between capturing B-mode frames and Doppler color or power mode frames, for example with the variation in the pulse repetition occurring during Doppler mode operation but not occurring during B-mode operation.

The digital pulse Doppler ultrasound system 404 includes a master clock or oscillator 412 which outputs a timing signal. The timing signal output by the master clock or oscillator 412 sets or is used to set a nominal pulse repetition frequency, that is the frequency at which ultrasound pulses repeat. In some implementations, the nominal pulse repetition frequency can be set by an operator, at least within some defined range. In other implementations, the nominal pulse repetition frequency may be a fixed characteristic of the particular digital pulse Doppler ultrasound system 404.

The transmit section 408 includes a variation circuit (VAR) 414 that introduces a variation in the clock signal provided by the master clock or oscillator 412, either directly or indirectly (e.g., via gate generator) introducing a variation from the nominal pulse repetition frequency into the drive signal used to drive the an ultrasound probe or transducer array 406 during a Doppler mode operation. The variation may be a variation in time or a variation in phase, and the variation is a variation over a period of time during the Doppler mode operation. The variation may, for example, be implemented via one or more delay circuits, which delay the clock signal. For example, a delay circuit may have an adjustable delay, or two or more different delay circuits, each with respective delays, may introduce delays of different durations to achieve the variation. The variation may be periodic, may follow a pattern, or may be pseudo-random, for instance produced via a pseudo-random number generator, also known as a random number generator (RNG). A periodic variation may have a period or frequency that is different from the nominal pulse repetition frequency. A periodic variation or variation that follows a pattern may be advantageously employed by the receive section 410. The variation is preferably at least one order of magnitude less than the nominal pulse repetition frequency, and more preferably two orders of magnitude, three orders of magnitude, four orders of magnitude, five orders of magnitude, or most preferably six orders of magnitude less than the nominal pulse repetition frequency.

The varied clock signal is supplied to a gate generator 416, which is communicatively coupled via an amplifier 418 to drive the ultrasound probe or transducer array 406. The varied clock signal is also supplied to the receive section 410, for example to a set of mixers 420, and a set of analog-to-digital converters (ADCs) 422.

The receive section 410 receives signals representative of the ultrasound energy returned from objects in the field of view of the ultrasound probe or transducer array 406, and an amplifier 424 of the receive section 410 amplifies the return signals. A matched filter 426 filters the amplified return signals. The set of mixers 420 then mix in the varied clock signal, and the results are analog-to-digital converted by ADCs 422. The output from the ADCs 422 are provided to a set of range gates 428 for digital signal processing.

Figure 5:
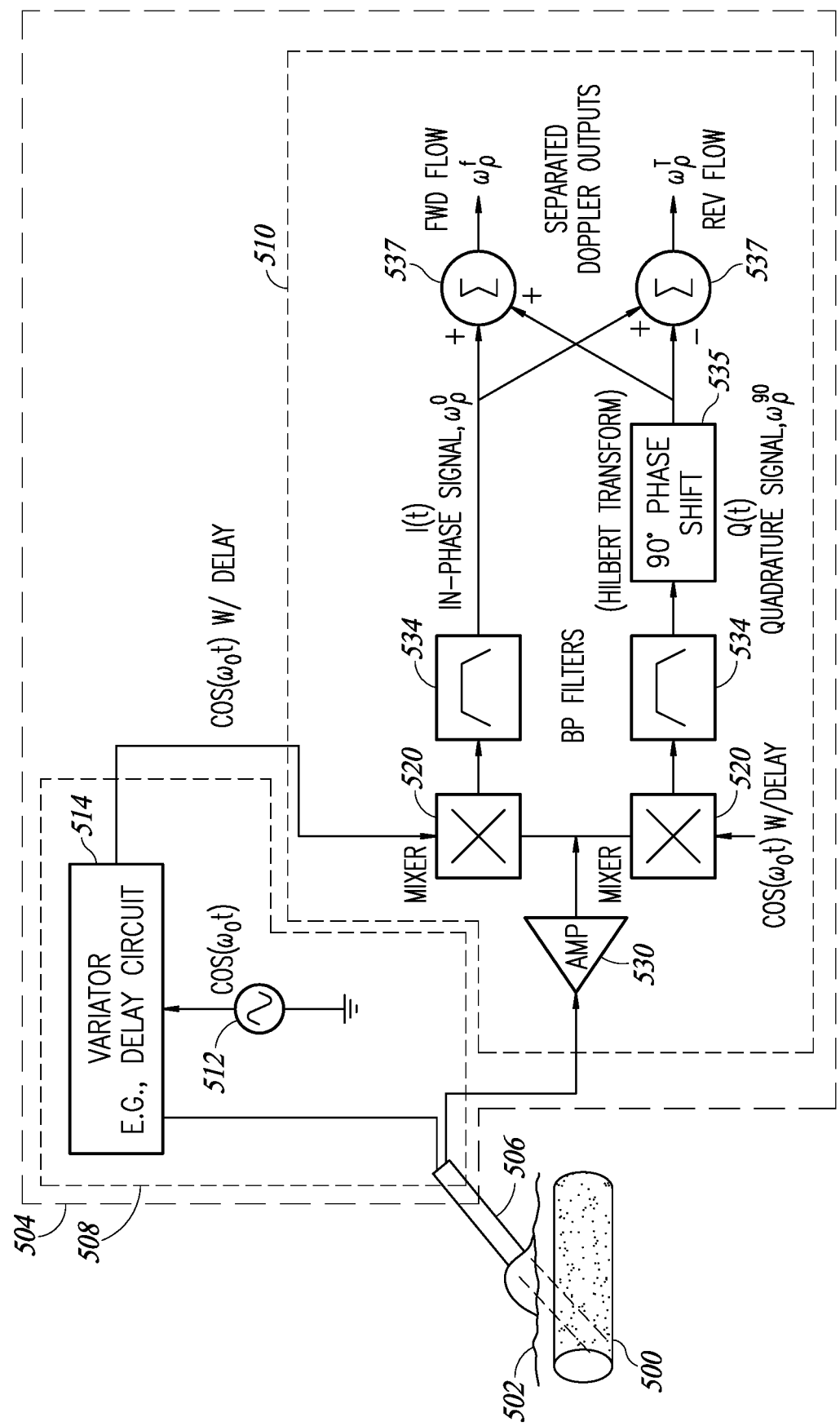
FIG. 5 is a schematic view of a continuous wave (CW) ultrasound imaging system according to at least one illustrated implementation, the CW ultrasound imaging system which introduces a variation from a nominal pulse repetition frequency into a drive signal that drives an ultrasound transducer, and which is operable to detect, in a Doppler mode (e.g., color Doppler mode) of operation, a twinkling artifact in the received return signal, the twinkling artifact resulting from interaction of the ultrasound signal having the varied pulse repetition frequency with at least a portion of a marker that is ultrasound reflective and which preferably has an irregular surface.

FIG. 5 shows a marker 500 implanted in bodily tissue 502, and a continuous wave Doppler ultrasound system 504 including an ultrasound probe or transducer array 506 positioned to detect the marker 500, according to at least one illustrated embodiment.

The continuous wave Doppler ultrasound system 504 includes a transmit section 508 and a receive section 510. The transmit section 508 generates a continuous (e.g., sine wave, cosine wave) signal and drives the ultrasound probe or transducer array 506 to emit ultrasound energy. The receive section 510 receives signals representative of the ultrasound energy returned from objects in the field of view of the ultrasound probe or transducer array 506, and processes the return signals based on one or more operational modes (e.g., A-mode, B-mode, M-mode, Doppler color mode, Doppler power mode). In some implementations, the continuous wave Doppler ultrasound system 504 will alternate between capturing B-mode frames and Doppler color or power mode frames, for example with the variation in the pulse repetition occurring during Doppler mode operation but not occurring during B-mode operation.

The continuous wave Doppler ultrasound system 504 includes a master clock or oscillator 512 which outputs a timing signal. The timing signal output by the master clock or oscillator 512 sets or is used to generate the continuous wave (e.g., sine wave, cosine wave). In some implementations, a frequency of the continuous wave can be set by an operator, at least within some defined range. In other implementations, the frequency of the continuous wave may be a fixed characteristic of the particular ultrasound system 504.

The transmit section 508 includes a variation circuit (VAR) 514 that introduces a variation in the continuous wave signal provided by the master clock or oscillator 512, either directly or indirectly introducing a variation from a nominal frequency of the continuous wave drive signal used to drive the ultrasound probe or transducer array 506 during a Doppler mode operation. The variation may be represented as a variation in time or a variation in phase, and the variation is a variation over a period of time during the Doppler mode operation. The variation may, for example, be implemented via one or more delay circuits, which delay the clock signal. For example, a delay circuit may have an adjustable delay, or two or more different delay circuits, each with respective delays, may introduce delays of different durations to achieve the variation. The variation may be periodic, may follow a pattern, or may be pseudo-random, for instance produced via a pseudo-random number generator, also known as a random number generator (RNG). A periodic variation may have a period or frequency that is different from the nominal pulse repetition frequency. A periodic variation or variation that follows a pattern may be advantageously employed by the receive section 510. The variation is preferably at least one order of magnitude less than the nominal pulse repetition frequency, and more preferably two orders of magnitude, three orders of magnitude, four orders of magnitude, five orders of magnitude, or most preferably six orders of magnitude less than the nominal pulse repetition frequency.

The varied continuous wave signal is also supplied to the receive section 510, for example to a set of mixers 520, which may be implemented in hardware, software and/or firmware.

The receive section 510 receives signals representative of the ultrasound energy returned from objects in the field of view of the ultrasound probe or transducer array 506, and an amplifier 530 of the receive section 510 amplifies the return signals. A matched filter 532 filters the amplified return signals. The set of mixers 520 then mix in the varied continuous wave signal, and the results are low pass filtered by a set of low pass filters 534. A phase shifter 535 phase shifts one of the signal paths, to provide for quadrature processing, and a set of summers 537 produce separated Doppler outputs (e.g., forward flow; reverse flow).

In any of the implementations of FIGS. 3, 4 and 5, an image captured during Doppler mode operation may be presented superimposed with an image captured during B-mode operation to facilitate visualization of the maker with respect to various anatomical features of the body.

Figure 6:
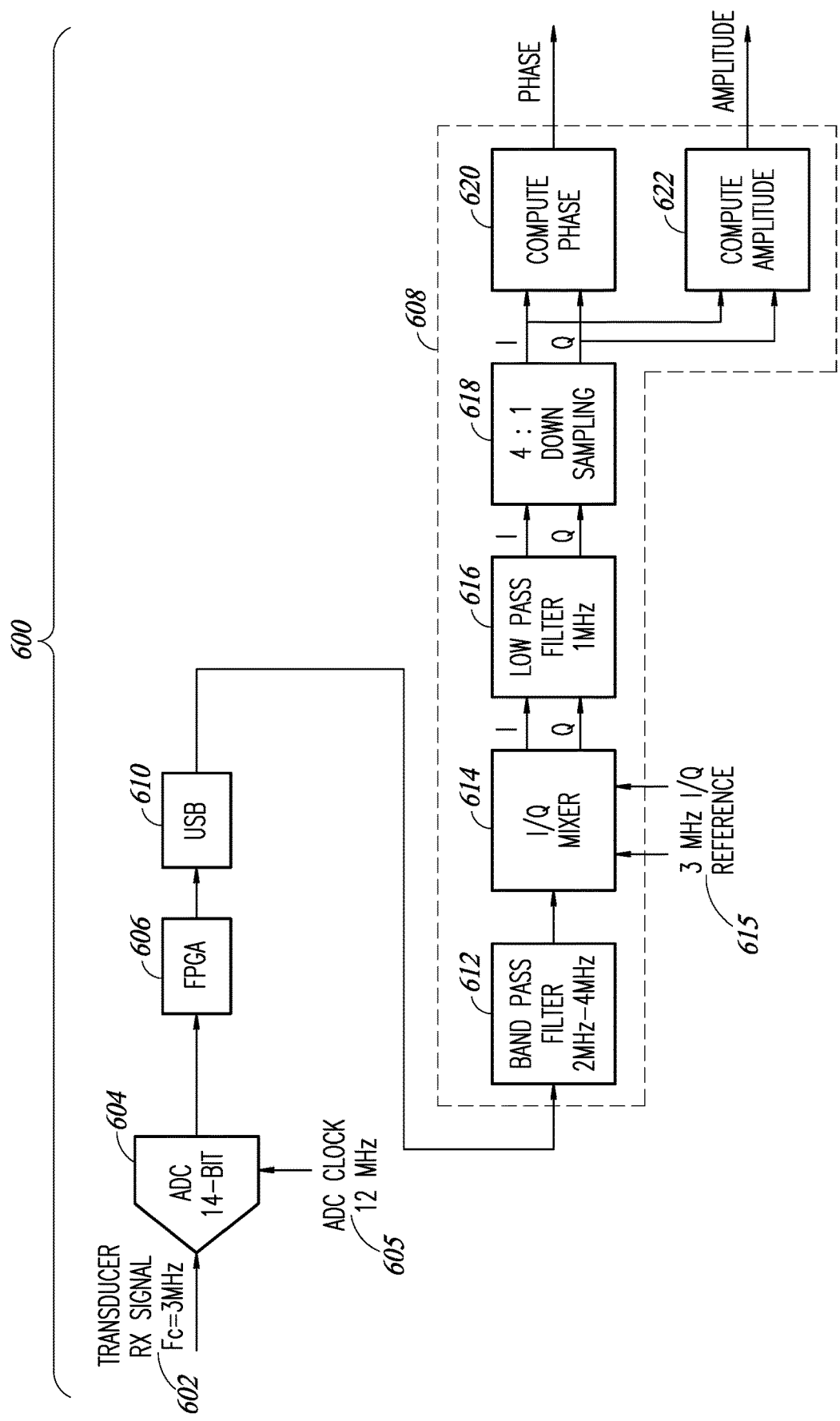
FIG. 6 is a block diagram of a signal processing algorithm which can be implemented in hardware, software and/or firmware, according to at least one illustrated implementation.

FIG. 6 shows a signal processing algorithm 600 which can be implemented in hardware, software and/or firmware, according to at least one illustrated implementation. The hardware may, for example include an analog-to-digital converter (ADC), field programmable gate array (FPGA), and one or more processor based computer systems that employs one or more processors and memory or other non-transitory storage media. The processor(s) may, for example, include one or more of: microprocessors, microcontrollers, central processing units (CPUs), digital signal processors (DSPs), graphics processing units (GPUs), applications specific integrated circuits (ASICs), field programmable gate arrays (FPGAs), and/or programmed logic controllers (PLCs), etc. The memory may, for example, include one or more of: read only memory (ROM), random access memory (RAM), EEPROMs, Flash memory, and/or registers, etc. The other non-transitory storage media may, for example, include one or more of: magnetic disks and associated magnetic disk drives, optical disks and associated optical disk drives, and/or solid state drives (SSDs), etc.

An analog transducer signal 602 is received from a transducer (not shown in FIG. 6). The received analog transducer signal 602 has a center frequency, for example a center frequency of 3 MHz.

The received analog transducer signal 602 is digitized, for example via an ADC 604. The ADC 604 may, for example take the form of a 14-Bit ADC with, for example, a 12 MHz sample clock 605.

The raw ADC sample data output by the ADC 604 is captured by an FPGA 606 (add FIG. 6), and transferred to a processor-based computer system (represented by broken-line box) 608, for example via a USB interface 610. Notably, the FPGA 606 just captures the ADC sample data and passes the ADC sample data to the processor-based computer system 608 without performing any operations on the ADC sample data.

Figure 7A:
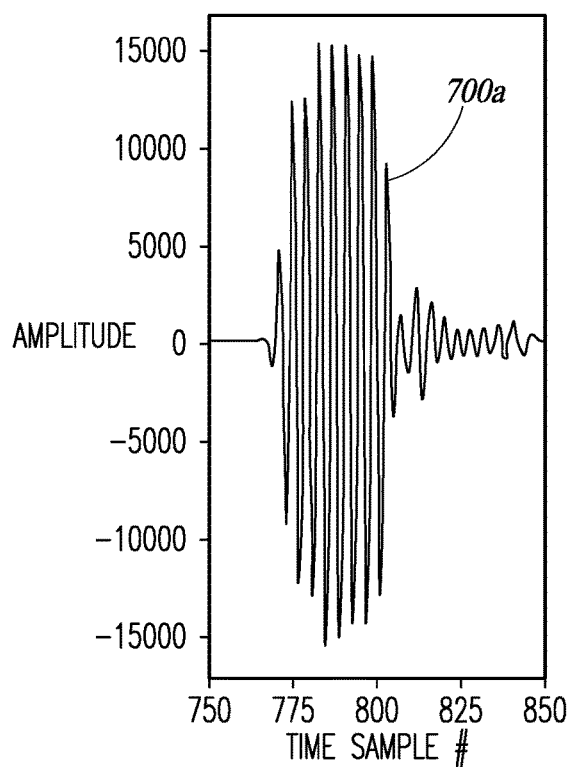
FIG. 7A is a graph showing an exemplary raw analog-to-digital (ADC) signal in a time domain produced by an ADC, according to at least one illustrated implementation.
Figure 7B:
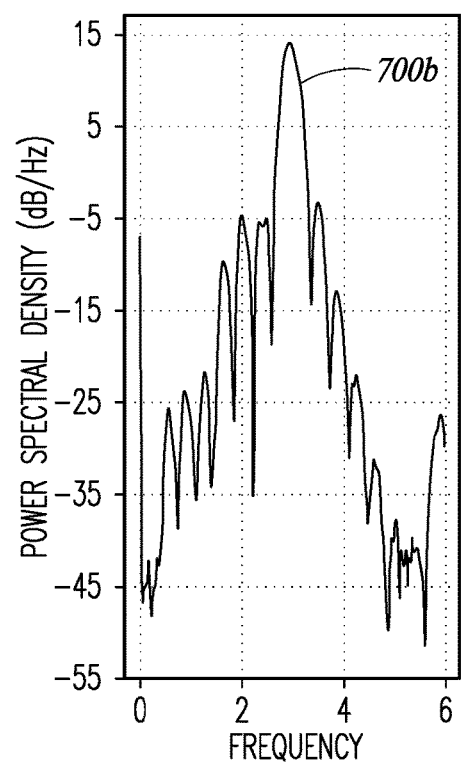
FIG. 7B is a graph showing an exemplary raw analog-to-digital (ADC) signal in a frequency domain produced by an ADC, according to at least one illustrated implementation.

FIGS. 7A and 7B illustrate an example of the raw ADC signals 700a, 700b in time and frequency domains, respectively. In particular, FIG. 7A is zoomed in on the raw ADC signal 700a from a 750th to 850th sample. FIG. 7B is a power spectral density estimate of the raw ADC signals 700b which is based on FFT. One can see how the maximum power is centered about 3 MHz, which is expected given that the Tx frequency is 3 MHz. At this point, the raw ADC signal has not been filtered.

Returning to FIG. 6, the processor-based computer system 608 may perform the remaining signal processing operations. For example, software written in Python may operate on the collected raw ADC samples provided via the FPGA 606.

In a first signal processing operation, the software executed by the processor-based computer system 608 may implement a band pass filter 612 to remove out-of-band noise before an I/Q Demodulation signal processing operation. The band pass filter 612 may, for example, have a pass band between 2 MHz to 4 MHz.

Figure 8A:
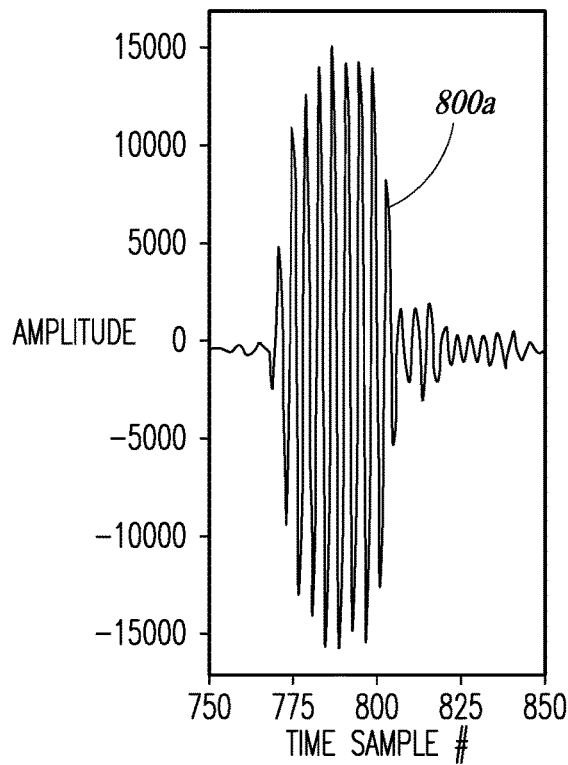
FIG. 8A is a graph showing an exemplary band-pass filtered ADC signal in the time domain after band-pass filtering the raw ADC signal, according to at least one illustrated implementation.
Figure 8B:
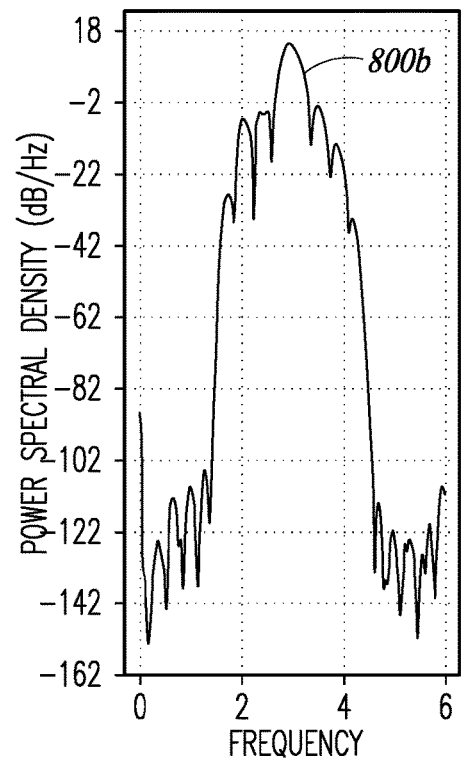
FIG. 8B is a graph showing an exemplary band-pass filtered ADC signal in the frequency domain after band-pass filtering the raw ADC signal, according to at least one illustrated implementation.

FIG. 8A illustrates a band-pass filtered ADC signal in the time domain 800a (limited to time samples 750 and 850 out of a total of 1600 taken) after band-pass filtering the raw ADC signal (FIG. 7A) for 2-4 MHz. FIG. 8B shows a band-passed filtered ADC signal in frequency domain 800b after band-pass filtering the raw ADC signal (FIG. 7B) for 2-4 MHz. Note how the frequency power in the range 0-2 and 4-6 MHz are greatly reduced when compared to that illustrated in FIGS. 7A and 7B.

Figure 9:
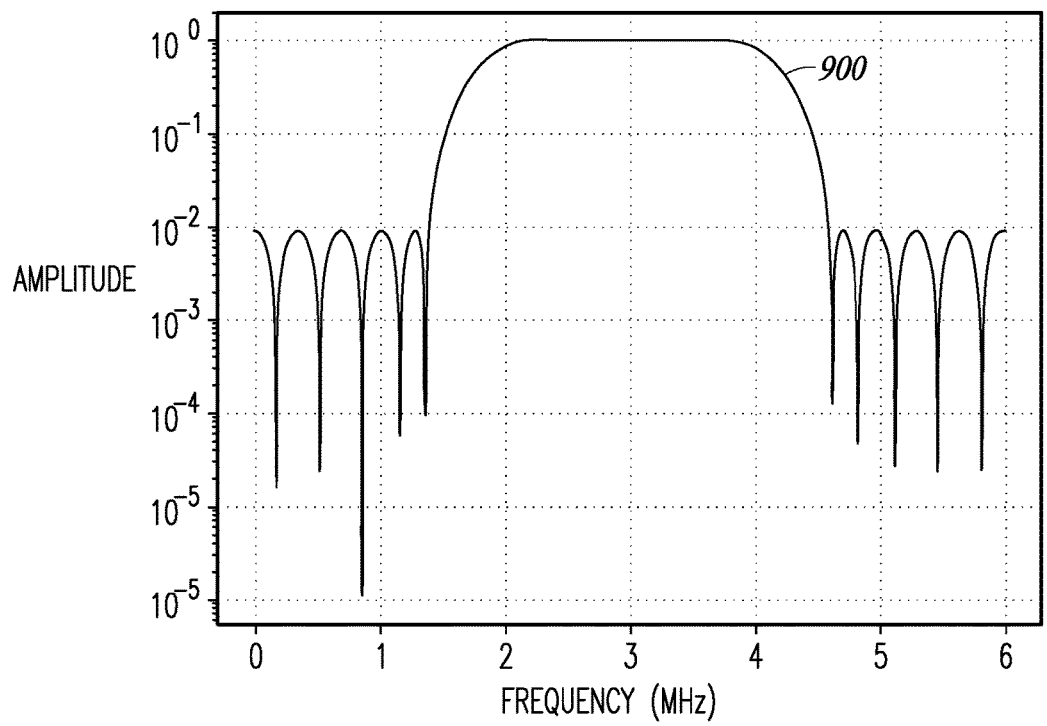
FIG. 9 is a graph showing a filter response for an exemplary band pass filter, according to at least one illustrated implementation.

FIG. 9 shows the filter response 900 for an exemplary band pass filter 612.

Returning to FIG. 6, the software executed by the processor-based computer system 608 may implement an I/Q mixer 614 to perform demodulation signal processing operations. The I/Q mixer 614 mixes the output of the band pass filter 612 with an I/Q reference signal, for example a 3 MHz I/Q reference signal 615. The frequency of the I/Q reference signal 615 may preferably be matched to a center frequency of the received transducer signal 602.

Figure 10A:
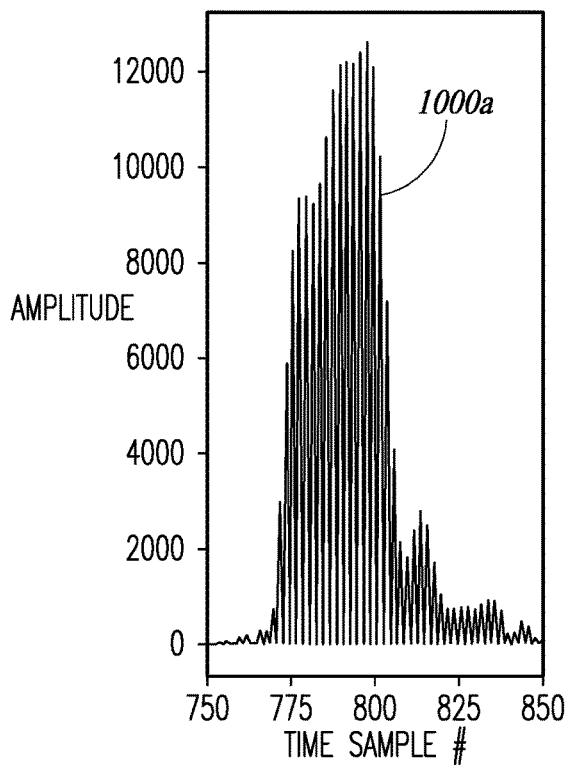
FIG. 10A is a graph showing an I/Q signal in a time domain output by an I/Q mixer after mixing with an I/Q reference signal, according to at least one illustrated implementation.
Figure 10B:
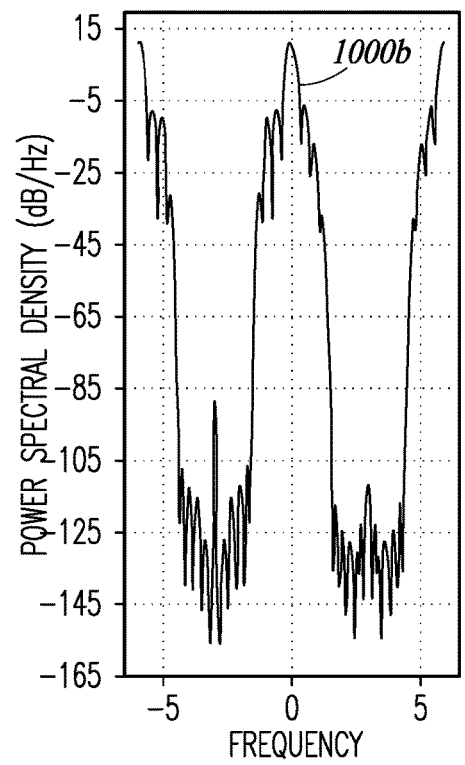
FIG. 10B is a graph showing an I/Q signal in the frequency domain output by an I/Q mixer after mixing with an I/Q reference signal, according to at least one illustrated implementation.

FIG. 10A shows an I/Q signal 1000a in the time domain output by the I/Q mixer 614 after mixing with an I/Q reference signal, containing the signal from the 750$^{th}$ to 850$^{th}$ sample. FIG. 10B shows a I/Q signal 1000b in the frequency domain output by the I/Q mixer 614 after mixing with an I/Q reference signal. The mixed I/Q signal is centered around zero since the I/Q reference signal matches the frequency of the received signal. Notably, there is a very slight asymmetry between negative and positive frequencies.

Returning to FIG. 6, the software executed by the processor-based computer system 608 may implement a low pass filter 616 to remove any double frequency components from the signal output by the I/Q Mixer 614, only keeping the baseband components. Applying a low pass filter obtains the envelope of the mixed signal. Notably, this is why the line in the time domain plot of FIG. 11A looks smooth unlike its counterpart in FIG. 10A). The low pass filter 616 may, for example, have a pass band set to 1 MHz.

Figure 11A:
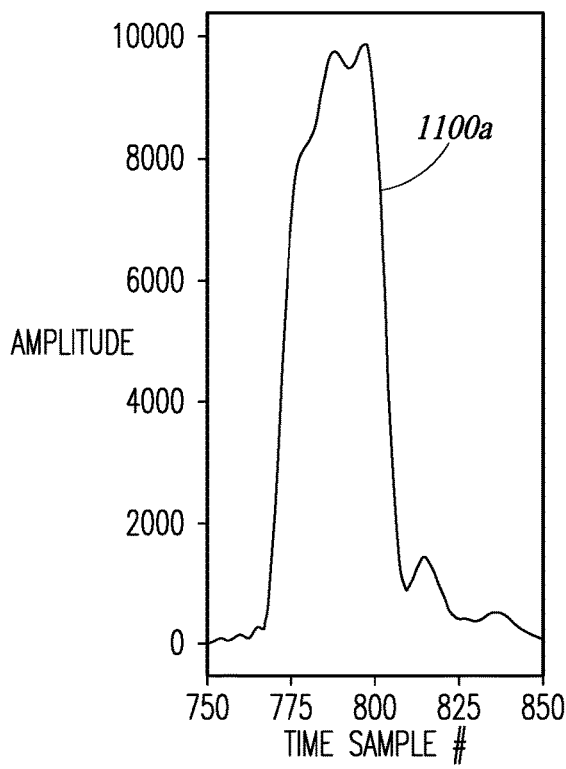
FIG. 11A is a graph showing a low passed filtered I/Q signal in the time domain output by the low pass filter, according to at least one illustrated implementation.

FIG. 11A shows a low passed filtered I/Q signal 1100a in the time domain output by the low pass filter 616.

Figure 11B:
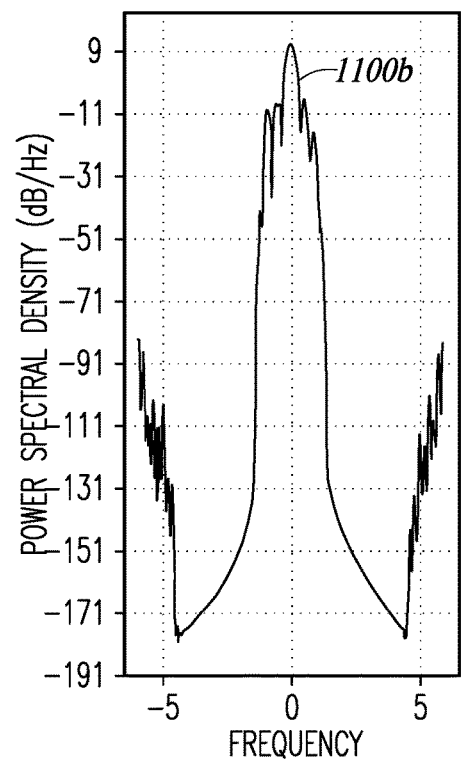
FIG. 11B is a graph showing a low passed filtered I/Q signal in the frequency domain output by the low pass filter, according to at least one illustrated implementation.

FIG. 11B shows a low passed filtered I/Q signal 1100b in the frequency domain output by the low pass filter 616.

Figure 12:
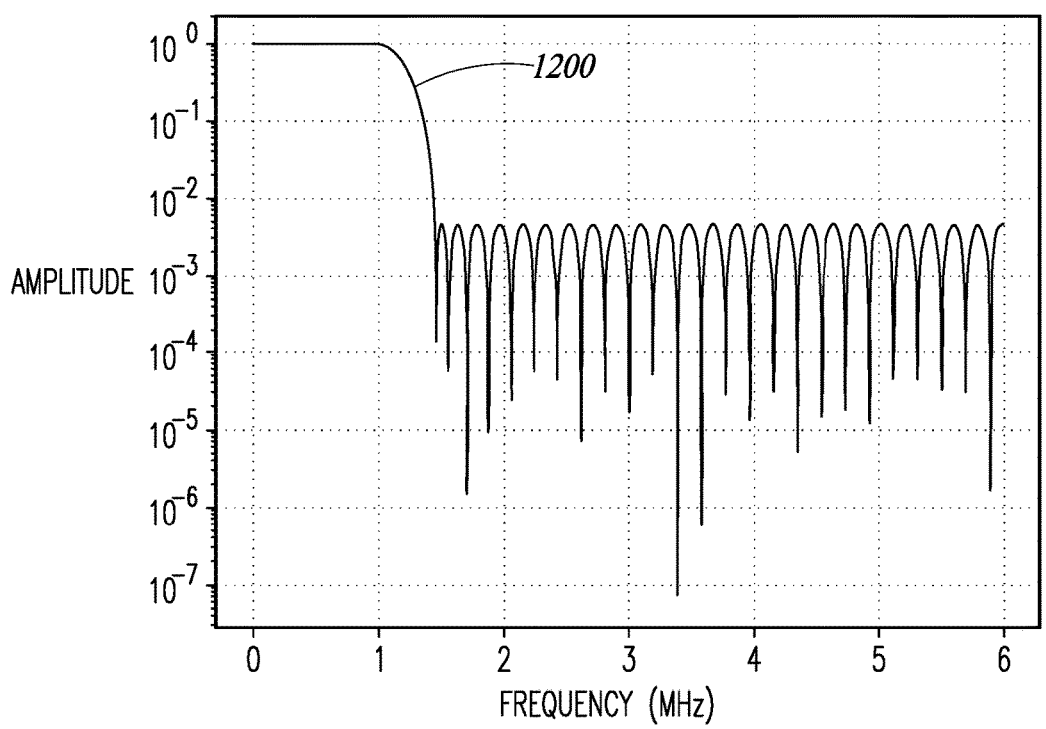
FIG. 12 is a graph showing a filter response of an exemplary low-pass filter that, for example, selects frequencies less than 1 MHz, according to at least one illustrated implementation.

FIG. 12 shows a filter 1200 response of an exemplary low-pass filter 616 that, for example, selects frequencies less than 1 MHz.

Returning to FIG. 6, the software executed by the processor-based computer system 608 may implement a down sampler 618 in order to reduce the data sample rate. The down sampler 618 may reduce the data sample rate from, for example 12 MHz to 3 MHz, for instance where the data output from the low pass filter 616 only has frequency components less than 1 MHz. Reducing the sample rate advantageously reduces the amount of data required for processing without reducing the information content.

Figure 13A:
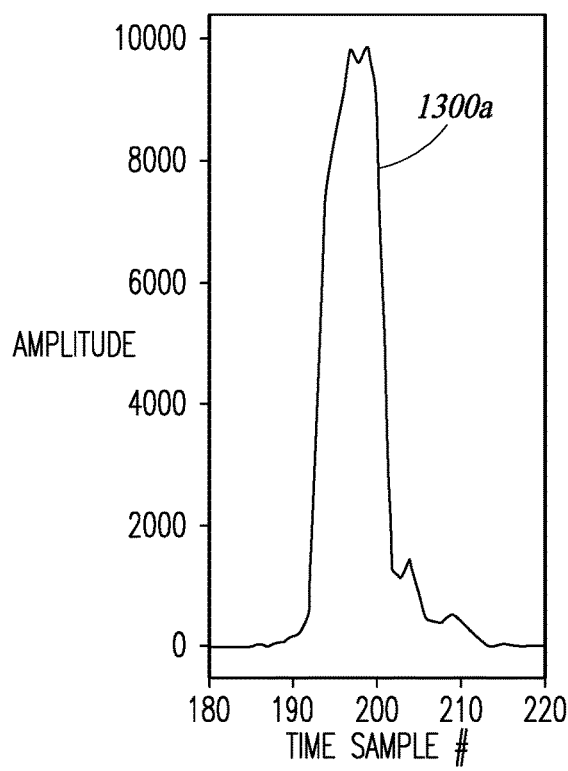
FIG. 13A is a graph showing a down sampled I/Q signal in the time domain, output by the down sampler, according to at least one illustrated implementation.
Figure 13B:
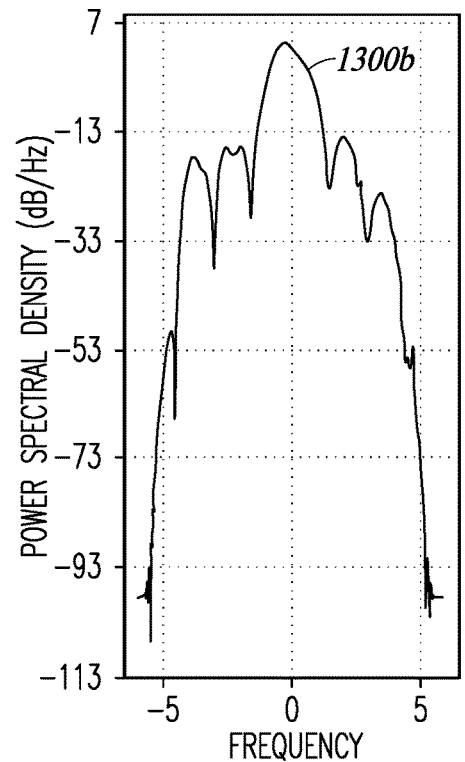
FIG. 13B is a graph showing a down sampled I/Q signal in the frequency domain, output by the down sampler, according to at least one illustrated implementation.

FIG. 13A shows the down sampled I/Q signal 1300a in the time domain, output by the down sampler 618. FIG. 13B shows the down sampled I/Q signal 1300b in the frequency domain, output by the down sampler 618. In the illustrated example, the low pass filtered I/Q data was advantageously down sampled by a factor of four.

Returning to FIG. 6, the software executed by the processor-based computer system 608 may implement a phase computation component or signal processing operation 620, in which a phase of the down sampled I/Q signal is computed for each sample point for the down sampled I/Q data.

Returning to FIG. 6, the software executed by the processor-based computer system 608 may implement an amplitude computation component or signal processing operation 622, in which an amplitude of the down sampled I/Q signal is computed for each sample point for the down sampled I/Q data.

Figure 14A:
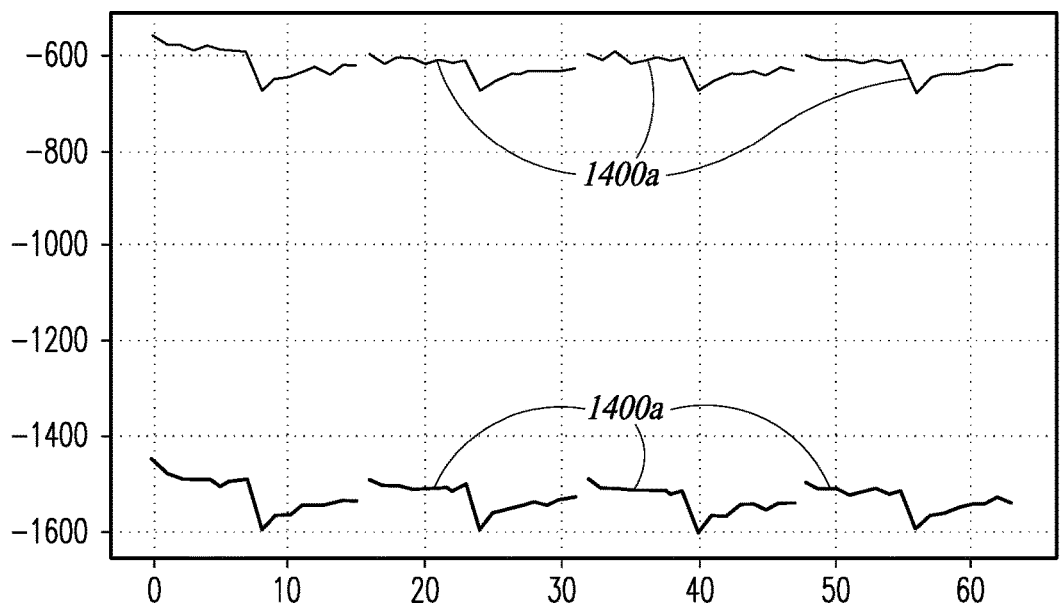
FIG. 14A is a graph showing downسampled I/Q data that results from the down sampling, according to at least one illustrated implementation.
Figure 14B:
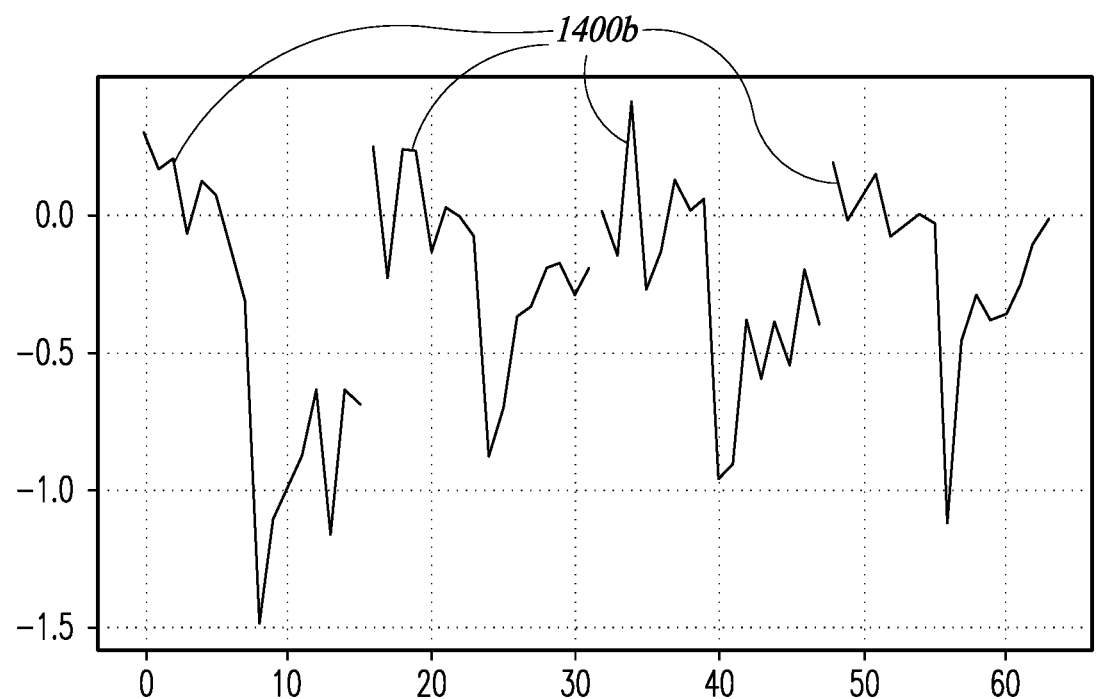
FIG. 14B is a graph showing a phase in degrees of the down sampled I/Q data, according to at least one illustrated implementation.
Figure 14C:
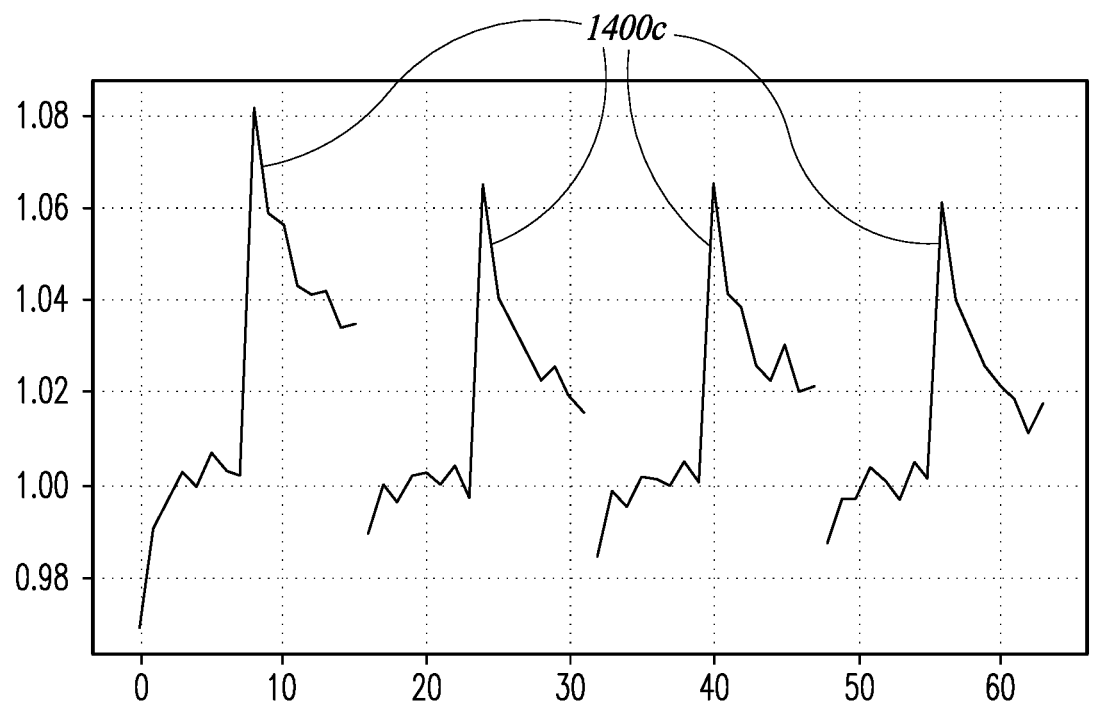
FIG. 14C is a graph showing a normalized amplitude of the down sampled I/Q data, according to at least one illustrated implementation.

FIG. 14A shows the down sampled I/Q data 1400a that results from the down sampling. FIG. 14B shows a plot of the phase in degrees 1400b of the down sampled I/Q data. FIG. 14C shows a plot of the normalized amplitude 1400c of the down sampled I/Q data. In this particular illustrated example, there is only a 10% range for amplitude and an approximately 1.5 degrees variation of phase.

EXAMPLES

Example 1. A method of operation in an ultrasound system, the method comprising:
generating a drive signal having a nominal pulse repetition frequency;
introducing a variation from the nominal frequency into the drive signal, the variation being at least one order of magnitude less than the nominal pulse repetition frequency;
supplying the drive signal with the introduced variation to the at least one ultrasound transducer to cause the at least one ultrasound transducer to emit the ultrasound signal having the variation from the nominal pulse repetition frequency;
emitting an ultrasound signal via at least one ultrasound transducer, the emitted ultrasound signal having a varied pulse repetition frequency, the varied pulse repetition frequency representing the variation from the nominal pulse repetition frequency; and
receiving a return signal via the at least one ultrasound transducer.

Example 2. The method of Example 1 wherein introducing the variation into the drive signal is in addition to any variation resulting from clock jitter, if any, of a master oscillator.

Example 3. The method of Example 2 wherein introducing the variation into the drive signal includes introducing a defined variation in pulse repetition frequency into the drive signal.

Example 4. The method of Example 3 wherein introducing a defined variation in pulse repetition frequency into the drive signal includes introducing a defined variation in pulse repetition frequency that changes over time in a defined pattern into the drive signal.

Example 5. The method of Example 2 wherein introducing the variation into the drive signal includes introducing a random variation in pulse repetition frequency into the drive signal.

Example 6. The method of Example 2 wherein introducing the variation into the drive signal includes introducing a delay into the drive signal by a delay circuit.

Example 7. The method of Example 1 wherein introducing a variation from the nominal frequency into the drive signal, the variation being at least one order of magnitude less than the nominal frequency includes introducing a variation from the nominal frequency into the drive signal, the variation being at least two orders of magnitude less than the nominal pulse repetition frequency.

Example 8. The method of Example 1 wherein introducing a variation from the nominal frequency into the drive signal, the variation being at least one order of magnitude less than the nominal frequency includes introducing a variation from the nominal frequency into the drive signal, the variation being at least three orders of magnitude less than the nominal pulse repetition frequency.

Example 9. The method of Example 1 wherein introducing a variation from the nominal frequency into the drive signal, the variation being at least one order of magnitude less than the nominal frequency includes introducing a variation from the nominal frequency into the drive signal, the variation being at least four orders of magnitude less than the nominal pulse repetition frequency.

Example 10. The method of Example 1 wherein introducing a variation from the nominal frequency into the drive signal, the variation being at least one order of magnitude less than the nominal frequency includes introducing a variation from the nominal frequency into the drive signal, the variation being at least five orders of magnitude less than the nominal pulse repetition frequency.

Example 11. The method of Example 1 wherein introducing a variation from the nominal frequency into the drive signal, the variation being at least one order of magnitude less than the nominal frequency includes introducing a variation from the nominal frequency into the drive signal, the variation being at least six orders of magnitude less than the nominal pulse repetition frequency.

Example 12. The method of any of Examples 1 through 11 wherein introducing a variation from the nominal frequency into the drive signal, the variation being at least one order of magnitude less than the nominal frequency includes introducing a variation from a nominal pulse repetition frequency into the drive signal.

Example 13. The method of any of Examples 1 through 11 wherein introducing a variation from the nominal frequency into the drive signal includes introducing a variation from a nominal pulse repetition frequency into the drive signal over a plurality of pulses emitted during a Doppler mode of operation during capture of one or more Doppler frames of ultrasound data.

Example 14. An ultrasound system, the comprising:
  at least one ultrasound transducer;
  a control system including at least one drive circuit, that in operation:
    generates a drive signal having a nominal pulse repetition frequency;
    introduces a variation from the nominal frequency into the drive signal; and
    causes the at least one ultrasound transducer to emit an ultrasound signal having a varied pulse repetition frequency, the varied pulse repetition frequency representing the variation from the nominal pulse repetition frequency.

Example 15. The ultrasound system of Example 14 wherein the variation introduced into the drive signal is in addition to any variation resulting from clock jitter, if any, of a master oscillator.

Example 16. The ultrasound system of Example 14 wherein to introduce the variation in pulse repetition frequency into the drive signal the control system introduces a defined variation in pulse repetition frequency into the drive signal.

Example 17. The ultrasound system of Example 14 wherein to introduce a defined variation in pulse repetition frequency into the drive signal the control system introduces a defined variation in pulse repetition frequency that changes over time in a defined pattern into the drive signal.

Example 18. The ultrasound system of Example 14 wherein to introduce the variation in pulse repetition frequency into the drive signal the control system introduces a random variation in pulse repetition frequency into the drive signal.

Example 19. The ultrasound system of Example 14 wherein to introduce the variation into the drive signal a delay circuit introduces a delay into the drive signal.

Example 20. The ultrasound system of Example 14 wherein to introduce a variation from the nominal frequency into the drive signal, the variation being at least one order of magnitude less than the nominal pulse repetition frequency, the control system introduces a variation from the nominal frequency into the drive signal, the variation at least two orders of magnitude less than the nominal pulse repetition frequency.

Example 21. The ultrasound system of Example 14 wherein to introduce a variation from the nominal frequency into the drive signal, the variation being at least one order of magnitude less than the nominal pulse repetition frequency, the control system introduces a variation from the nominal frequency into the drive signal, the variation at least three orders of magnitude less than the nominal pulse repetition frequency.

Example 22. The ultrasound system of Example 14 wherein to introduce a variation from the nominal frequency into the drive signal, the variation being at least one order of magnitude less than the nominal pulse repetition frequency, the control system introduces a variation from the nominal frequency into the drive signal, the variation in at least four orders of magnitude less than the nominal pulse repetition frequency.

Example 23. The ultrasound system of Example 14 wherein to introduce a variation from the nominal frequency into the drive signal, the variation being at least one order of magnitude less than the nominal pulse repetition frequency, the control system introduces a variation from the nominal frequency into the drive signal, the variation in at least five orders of magnitude less than the nominal pulse repetition frequency.

Example 24. The ultrasound system of Example 14 wherein to introduce a variation from the nominal frequency into the drive signal, the variation being at least one order of magnitude less than the nominal pulse repetition frequency, the control system introduces a variation from the nominal frequency into the drive signal, the variation in at least six orders of magnitude less than the nominal pulse repetition frequency.

Example 25. The ultrasound system of Example 14 wherein the at least one ultrasound transducer is coupled to the control system to provide signals to the control system, the signals representative of return signals received by the at least one ultrasound transducer, and the control system is operable to detect, in a color Doppler mode of operation, a twinkling artifact in the received return signal, the twinkling artifact resulting from interaction of the ultrasound signal having the varied pulse repetition frequency with at least a portion of a marker that is ultrasound reflective and has an irregular surface.

Example 26. The ultrasound system of any of Examples 14 through 23 wherein to introduce a variation from the nominal frequency into the drive signal the control system introduces a variation from a variation from a nominal pulse repetition frequency into the drive signal.

Example 27. The ultrasound system of any of Examples 14 through 23 wherein to introduce a variation from the nominal frequency into the drive signal the control system introduce a variation from a nominal pulse repetition frequency into the drive signal over a plurality of pulses emitted during a Doppler mode of operation during capture of a Doppler frame of ultrasound data.

Example 28. A method employing an ultrasound system, the method comprising:
directing an ultrasound signal toward a portion of bodily tissue containing a marker, the ultrasound signal characterized by a nominal pulse repetition frequency, and having an actual pulse repetition frequency which varies over time from the nominal pulse repetition frequency;
receiving a return signal from the portion of bodily tissue via the at least one ultrasound transducer;
detecting a resonance of at least a portion of the marker induced by the ultrasound signal in the received return signal as a twinkling artifact in a color Doppler mode of operation of the ultrasound system; and
localizing the marker in bodily tissue based at least in part on the twinkling artifact in a color Doppler mode of operation.

Example 29. The method of Example 28, further comprising:
generating the ultrasound signal via at least one ultrasound transducer, the ultrasound signal having a nominal frequency over a period of time, the ultrasound signal further having a variation in pulse repetition frequency from the nominal pulse repetition frequency, the variation in frequency at least one or more orders of magnitude less than the nominal pulse repetition frequency.

Example 30. The method of Example 28, further comprising:
generating the ultrasound signal via at least one ultrasound transducer, the ultrasound signal having a nominal pulse repetition frequency over a period of time, the ultrasound signal further having a variation in pulse repetition frequency from the nominal pulse repetition frequency, the variation in frequency at least one or more orders of magnitude less than the nominal pulse repetition frequency.

Example 31. The method of Example 30 wherein generating the ultrasound signal includes:
generating a drive signal having the nominal pulse repetition frequency;
introducing the variation in frequency into the drive signal; and
supplying the drive signal with the introduced variation to the at least one ultrasound transducer to cause the at least one ultrasound transducer to emit the ultrasound signal having the variation in pulse repetition frequency from the nominal pulse repetition frequency.

Example 32. The method of Example 31 wherein introducing the variation in frequency into the drive signal includes introducing a variation from the nominal pulse repetition frequency into the drive signal over a plurality of pulses emitted during a Doppler mode of operation during capture of a Doppler frame of ultrasound data.

Example 33. The method of any of Examples 28 through 32 wherein directing an ultrasound signal toward a portion of bodily tissue containing a marker includes directing an ultrasound signal emitted by the at least one ultrasound transducer toward a portion of bodily tissue containing a marker, the maker comprising a hydrogel and a plurality of ultrasound reflective elements carried by the hydrogel.

Example 34. The method of any of Examples 28 through 32 wherein directing an ultrasound signal toward a portion of bodily tissue containing a marker includes directing an ultrasound signal toward a portion of bodily tissue containing a marker comprising an at least partially cross-linked hydrogel and a plurality of hollow shells at least temporarily encased by the at least partially cross-linked hydrogel, each of the hollow shells having a respective outer wall that forms a cavity, the outer wall having an irregular outer surface, and the cavity devoid of perfluorocarbon.

Example 35. A method of operation in an ultrasound system, the method comprising:
generating a drive signal via a master oscillator, the drive signal having a nominal pulse repetition frequency;
introducing a variation in a pulse repetition frequency of the drive signal with respect to the nominal pulse repetition frequency; and
driving at least one ultrasound transducer via the drive signal with the introduced variation in the pulse repetition frequency.

Example 36. The method of Example 35 wherein introducing the variation in pulse repetition frequency into the drive signal includes introducing a defined variation in pulse repetition frequency into the drive signal.

Example 37. The method of Example 35 wherein introducing a defined variation in pulse repetition frequency into the drive signal includes introducing a defined variation in pulse repetition frequency that changes over time in a defined pattern into the drive signal.

Example 38. The method of Example 35 wherein introducing the variation in pulse repetition frequency into the drive signal includes introducing a random variation in pulse repetition frequency into the drive signal.

Example 39. The method of Example 35 wherein introducing the variation in pulse repetition frequency into the drive signal includes introducing a variation in pulse repetition frequency that is at least two orders of magnitude less than the nominal pulse repetition frequency.

Example 40. The method of Example 35 wherein introducing the variation in pulse repetition frequency into the drive signal includes introducing a variation in pulse repetition frequency via a gate generator of the ultrasound system.

Example 41. The method of Example 35, further comprising:
directing an ultrasound signal emitted by the at least one ultrasound transducer toward a portion of bodily tissue containing a marker, the maker comprising a hydrogel and a plurality of ultrasound reflective elements carried by the hydrogel.

Example 42. The method of any of Examples 35 through 41, further comprising:
directing an ultrasound signal emitted by the at least one ultrasound transducer toward a portion of bodily tissue containing a marker includes directing an ultrasound signal emitted by the at least one ultrasound transducer toward a portion of bodily tissue containing a marker, the maker comprising a hydrogel and a plurality of ultrasound reflective elements carried by the hydrogel.

Example 43. The method of any of Examples 35 through 41, further comprising:
directing an ultrasound signal emitted by the at least one ultrasound transducer toward a portion of bodily tissue containing a marker, the maker comprising an at least partially cross-linked hydrogel and a plurality of hollow shells at least temporarily encased by the at least partially cross-linked hydrogel, each of the hollow shells having a respective outer wall that forms a cavity, the outer wall having an irregular outer surface, and the cavity devoid of perfluorocarbon.

Example 44. The method of any of Examples 35 through 43 wherein introducing a variation in a pulse repetition frequency of the drive signal with respect to the nominal pulse repetition frequency includes introducing a variation in the pulse repetition frequency over a plurality of pulses emitted during a Doppler mode of operation during capture of one or more Doppler frames of ultrasound data.

Example 45. A marker, comprising:
at least one hollow shell having at least one outer wall that forms a cavity, the cavity devoid of perfluorocarbon.

Example 46. The marker of Example 45 wherein the cavity of the at least one hollow shell contains a gas.

Example 47. The marker of Example 45 wherein the cavity of the at least one hollow shell contains air.

Example 48. The marker of Example 45 wherein the cavity of the at least one hollow shell contains an inert gas.

Example 49. The marker of Example 45 wherein the at least one hollow shell comprises a silica.

Example 50. The marker of Example 45 wherein the at least one hollow shell consists of a silica.

Example 51. The marker of Example 45 wherein the at least one hollow shell is porous.

Example 52. The marker of Example 51 wherein the at least one hollow shell comprises a hydrophobic coating that at least temporarily seals one or more pores thereof.

Example 53. The marker of Example 45 wherein the at least one hollow shell comprises a plurality of hollow shells.

Example 54. The marker of Example 53, further comprising:
a hydrogel that binds the plurality of hollow shells together.

Example 55. The marker of Example 54 wherein the hydrogel is an at least partially cross-linked hydrogel.

Example 56. The marker of any of Examples 50 or 55 wherein the hydrogel is a gelatin.

Example 57. The marker of any of Examples 45 through 55 wherein the hollow shell has a rough outer surface.

Example 58. The marker of any of Examples 45 through 55 wherein the hollow shell is highly reflective of ultrasound.

Example 59. The marker of any of Examples 45 through 55 wherein the hollow shell has a rough outer surface and the hollow shell is highly reflective of ultrasound.

Example 60. A marker, comprising:
a hydrogel carrier; and
a plurality of ultrasound reflective elements carried by the hydrogel carrier, the ultrasound reflective elements having a high reflectivity of ultrasound, an irregular outer surface, and being solid particles or porous and non-spherical particles.

Example 61. The marker of Example 60 wherein the hydrogel carrier binds the plurality of ultrasound reflective elements together.

Example 62. The marker of Example 61 wherein the hydrogel carrier is an at least partially cross-linked hydrogel.

Example 63. The marker of any of Examples 61 or 62 wherein the hydrogel carrier comprises a gelatin.

Example 64. The marker of any of Examples 61 or 62 wherein each of the ultrasound reflective elements of the plurality of ultrasound reflective elements comprises a respective hollow shell having at least one outer wall that forms a cavity, the cavity devoid of perfluorocarbon.

Example 65. The marker of Example 60 wherein the cavity of the hollow shell contains a gas.

Example 66. The marker of Example 60 wherein the cavity of the hollow shell contains air.

Example 67. The marker of Example 60 wherein the cavity of the hollow shell contains an inert gas.

Example 68. The marker of Example 60 wherein the hollow shell comprises a silica.

Example 69. The marker of Example 60 wherein the hollow shell consists of a silica.

Example 70. The marker of Example 60 wherein the hollow shell is porous.

Example 71. The marker of Example 60 wherein each of the ultrasound reflective elements of the plurality of ultrasound reflective elements comprises a respective a hydrophobic coating that at least temporarily seals one or more pores thereof.

Example 72. The marker of any of Examples 60 through 62 or Examples 64 through 71 wherein the hollow shell has a rough outer surface.

Example 73. The marker of any of Examples 60 through 62 or Examples 64 through 71 wherein the hollow shell is highly reflective of ultrasound.

Example 74. The marker of any of Examples 60 through 62 or Examples 64 through 71 wherein the hollow shell has a rough outer surface and the hollow shell is highly reflective of ultrasound.

Example 75. A kit, comprising:
at least one marker, the at least one marker comprising: a plurality of hollow shells having at least one outer wall that forms a cavity, and a hydrogel that binds the plurality of hollow shells together; and
an ultrasound system, the ultrasound system comprising: at least one ultrasound transducer, and a control system including at least one drive circuit, that in operation: generates a drive signal having a nominal pulse repetition frequency; introduces a variation from the nominal frequency into the drive signal; and causes the at least one ultrasound transducer to emit an ultrasound signal having a varied pulse repetition frequency, the varied pulse repetition frequency representing the variation from the nominal pulse repetition frequency.

Example 76. The kit of Example 75 wherein to introduce a variation from the nominal frequency into the drive signal the control system introduce a variation from a nominal pulse repetition frequency into the drive signal over a plurality of pulses emitted during a Doppler mode of operation during capture of a Doppler frame of ultrasound data.

Example 77. The kit of Example 75 wherein the cavities of the hollow shells contain a gas.

Example 78. The kit of Example 75 wherein the cavities of the hollow shells contain air and are devoid of perfluorocarbon.

Example 79. The kit of Example 75 wherein the hollow shells comprise a silica.

Example 80. The kit of Example 75 wherein the hollow shells consist of a silica.

Example 81. The kit of Example 75 wherein the hollow shells are porous.

Example 82. The kit of Example 76 wherein the hollow shells each bear a hydrophobic coating that at least temporarily seals one or more pores thereof.

Example 83. The kit of Example 77 wherein the hydrogel is an at least partially cross-linked hydrogel.

Example 84. The kit of any of Examples 82 or 83 wherein the hydrogel is a gelatin.

Example 85. The kit of any of Examples 75 through 83 wherein the hollow shell has a rough outer surface.

Example 86. The kit of any of Examples 75 through 83 wherein the hollow shell is highly reflective of ultrasound.

Example 87. The kit of any of Examples 75 through 83 wherein the hollow shell has a rough outer surface and the hollow shell is highly reflective of ultrasound.

Example 88. The kit of any of Examples 75 through 83 wherein to introduce a variation from the nominal frequency into the drive signal the control system introduces a variation from a variation from a nominal pulse repetition frequency into the drive signal.

The foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Those of skill in the art will recognize that many of the methods or algorithms set out herein may employ additional acts, may omit some acts, and/or may execute acts in a different order than specified.

In addition, those skilled in the art will appreciate that the mechanisms taught herein are capable of being distributed as a program product in a variety of forms, and that an illustrative implementation applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory.

The various implementations described above can be combined to provide further implementations. U.S. patent application 60/955,678; U.S. patent application 61/034,468; U.S. patent application Ser. No. 12/673,224 (now U.S. Pat. No. 8,440,229); International patent application PCT/US2008/072972; U.S. patent application Ser. No. 13/866,940 (now U.S. Pat. No. 9,220,685); U.S. patent application Ser. No. 15/722,436; U.S. patent application 61/707,794; International patent application PCT/US2013/062436; U.S. patent application Ser. No. 15/706,446; U.S. patent application 62/135,653; U.S. patent application Ser. No. 15/559,764; International patent application PCT/US2016/23492; U.S. patent application 62/483,274; U.S. patent application 62/645,677; U.S. patent application Ser. No. 15/946,479; International patent application PCT/US2018/26291; and U.S. patent application 62/892,952, are each incorporated herein by reference in their entirety. Aspects of the implementations can be modified, if necessary, to employ systems, circuits and concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

I claim:

1. A method of operation in an ultrasound system, the method comprising:
   generating a drive signal having a nominal pulse repetition frequency;
   introducing a variation from the nominal pulse repetition frequency into the drive signal, the variation being at least one order of magnitude less than the nominal pulse repetition frequency;
   supplying the drive signal with the introduced variation to at least one ultrasound transducer to cause the at least one ultrasound transducer to emit an ultrasound signal having the variation from the nominal pulse repetition frequency;
   emitting the ultrasound signal via at least one ultrasound transducer, the emitted ultrasound signal having a varied pulse repetition frequency, the varied pulse repetition frequency representing the variation from the nominal pulse repetition frequency;
   receiving a return signal via the at least one ultrasound transducer;
   detecting a resonance of at least a portion of a marker induced by the ultrasound signal in the received return signal as a twinkling artifact in a color Doppler mode of operation of the ultrasound system; and
   localizing the marker in bodily tissue based at least in part on the twinkling artifact in a color Doppler mode of operation.

2. The method of claim 1 wherein introducing the variation into the drive signal is in addition to any variation resulting from clock jitter, if any, of a master oscillator.

3. The method of claim 2 wherein introducing the variation into the drive signal includes introducing a defined variation in pulse repetition frequency into the drive signal.

4. The method of claim 3 wherein introducing the defined variation in pulse repetition frequency into the drive signal includes introducing a defined variation in pulse repetition frequency that changes over time in a defined pattern into the drive signal.

5. The method of claim 2 wherein introducing the variation into the drive signal includes introducing a random variation in pulse repetition frequency into the drive signal.

6. The method of claim 2 wherein introducing the variation into the drive signal includes introducing a delay into the drive signal by a delay circuit.

7. The method of claim 1 wherein introducing the variation from the nominal pulse repetition frequency into the drive signal, the variation being at least one order of magnitude less than the nominal pulse repetition frequency includes introducing a variation from the nominal pulse repetition frequency into the drive signal, the variation being at least two orders of magnitude less than the nominal pulse repetition frequency.

8. The method of claim 1 wherein introducing the variation from the nominal pulse repetition frequency into the drive signal, the variation being at least one order of magnitude less than the nominal pulse repetition frequency includes introducing a variation from the nominal pulse repetition frequency into the drive signal, the variation being at least three orders of magnitude less than the nominal pulse repetition frequency.

9. The method of claim 1 wherein introducing the variation from the nominal pulse repetition frequency into the drive signal, the variation being at least one order of magnitude less than the nominal pulse repetition frequency includes introducing a variation from the nominal pulse repetition frequency into the drive signal, the variation being at least four orders of magnitude less than the nominal pulse repetition frequency.

10. The method of claim 1 wherein introducing the variation from the nominal pulse repetition frequency into the drive signal, the variation being at least one order of magnitude less than the nominal pulse repetition frequency includes introducing a variation from the nominal pulse repetition frequency into the drive signal, the variation being at least five orders of magnitude less than the nominal pulse repetition frequency.

11. The method of claim 1 wherein introducing the variation from the nominal pulse repetition frequency into the drive signal, the variation being at least one order of magnitude less than the nominal pulse repetition frequency includes introducing a variation from the nominal pulse repetition frequency into the drive signal, the variation being at least six orders of magnitude less than the nominal pulse repetition frequency.

12. The method of claim 1 wherein introducing the variation from the nominal pulse repetition frequency into the drive signal, the variation being at least one order of magnitude less than the nominal pulse repetition frequency includes introducing a variation from the nominal pulse repetition frequency into the drive signal over at least one pulse emitted during a Doppler mode of operation during capture of a respective Doppler frame of ultrasound data.

13. The method of claim 1 wherein introducing the variation from the nominal pulse repetition frequency into the drive signal includes introducing a variation from the nominal pulse repetition frequency into the drive signal over a plurality of pulses emitted during a Doppler mode of operation during capture of one or more Doppler frames of ultrasound data.

14. An ultrasound system, the ultrasound system comprising:
    at least one ultrasound transducer;
    a control system including at least one drive circuit, that in operation:
    generates a drive signal having a nominal pulse repetition frequency;
    introduces a variation from the nominal pulse repetition frequency into the drive signal; and
    causes the at least one ultrasound transducer to emit an ultrasound signal having a varied pulse repetition frequency, the varied pulse repetition frequency representing the variation from the nominal pulse repetition frequency; and
    wherein the at least one ultrasound transducer is coupled to the control system to provide signals to the control system, the signals representative of return signals received by the at least one ultrasound transducer, and the control system is operable to detect, in a color Doppler mode of operation, a twinkling artifact in the received return signal, the twinkling artifact resulting from interaction of the ultrasound signal having the varied pulse repetition frequency with at least a portion of a marker that is ultrasound reflective and has an irregular surface.

15. The ultrasound system of claim 14 wherein the variation introduced into the drive signal is in addition to any variation resulting from clock jitter, if any, of a master oscillator.

16. The ultrasound system of claim 14 wherein to introduce the variation from the nominal pulse repetition frequency into the drive signal the control system introduces a defined variation from the nominal pulse repetition frequency into the drive signal.

17. The ultrasound system of claim 14 wherein to introduce the defined variation from the nominal pulse repetition frequency into the drive signal the control system introduces a defined variation from the nominal pulse repetition frequency that changes over time in a defined pattern into the drive signal.

18. The ultrasound system of claim 14 wherein to introduce the variation from the nominal pulse repetition frequency into the drive signal the control system introduces a random variation from the nominal pulse repetition frequency into the drive signal.

19. The ultrasound system of claim 14 wherein to introducing the variation from the nominal pulse repetition frequency into the drive signal a delay circuit introduces a delay into the drive signal.

20. The ultrasound system of claim 14 wherein to introducing the variation from the nominal pulse repetition frequency into the drive signal, the variation being at least one order of magnitude less than the nominal pulse repetition frequency, the control system introduces a variation from the nominal pulse repetition frequency into the drive signal, the variation being at least two orders of magnitude less than the nominal pulse repetition frequency.

21. The ultrasound system of claim 14 wherein to introducing the variation from the nominal pulse repetition frequency into the drive signal, the variation being at least one order of magnitude less than the nominal pulse repetition frequency, the control system introduces a variation from the nominal pulse repetition frequency into the drive signal, the variation being at least three orders of magnitude less than the nominal pulse repetition frequency.

22. The ultrasound system of claim 14 wherein to introducing the variation from the nominal pulse repetition frequency into the drive signal, the variation being at least one order of magnitude less than the nominal pulse repetition frequency, the control system introduces a variation from the nominal pulse repetition frequency into the drive signal, the variation being at least four orders of magnitude less than the nominal pulse repetition frequency.

23. The ultrasound system of claim 14 wherein to introducing the variation from the nominal pulse repetition frequency into the drive signal, the variation being at least one order of magnitude less than the nominal pulse repetition frequency, the control system introduces a variation from the nominal pulse repetition frequency into the drive signal, the variation being at least five orders of magnitude less than the nominal pulse repetition frequency.

24. The ultrasound system of claim 14 wherein to introducing the variation from the nominal pulse repetition frequency into the drive signal, the variation being at least one order of magnitude less than the nominal pulse repetition frequency, the control system introduces a variation from the nominal pulse repetition frequency into the drive signal, the variation being at least six orders of magnitude less than the nominal pulse repetition frequency.

25. The ultrasound system of claim 14 wherein to introducing the variation from the nominal pulse repetition frequency into the drive signal the control system introduces a variation from the nominal pulse repetition frequency into the drive signal over at least one pulse emitted during a Doppler mode of operation during capture of a respective Doppler frame of ultrasound data.

26. The ultrasound system of claim 14 wherein to introduce a variation from the nominal pulse repetition frequency into the drive signal the control system introduce a variation from the nominal pulse repetition frequency into the drive signal over a plurality of pulses emitted during a Doppler mode of operation during capture of a Doppler frame of ultrasound data.

* * * * *